(12) United States Patent
Coats et al.

(10) Patent No.: US 6,524,605 B1
(45) Date of Patent: Feb. 25, 2003

(54) BIORATIONAL REPELLENTS OBTAINED FROM TERPENOIDS FOR USE AGAINST ARTHROPODS

(75) Inventors: Joel R. Coats, Ames, IA (US); Christopher J. Peterson, Ames, IA (US); Junwei Zhu, Ames, IA (US); Thomas C. Baker, Ames, IA (US); Leah T. Nemetz, Two Rivers, WI (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/635,030

(22) Filed: Aug. 4, 2000

Related U.S. Application Data

(60) Provisional application No. 60/147,679, filed on Aug. 6, 1999, and provisional application No. 60/150,051, filed on Aug. 20, 1999.

(51) Int. Cl.[7] .................. A01N 25/34; A01N 25/00; A01M 5/00; A01M 7/00

(52) U.S. Cl. .................. 424/408; 424/405; 43/132.1

(58) Field of Search .................. 424/408, 405; 43/132.1

(56) References Cited

U.S. PATENT DOCUMENTS

| | | | | |
|---|---|---|---|---|
| 4,882,873 A | * | 11/1989 | Purnell | 43/132.1 |
| 5,662,914 A | * | 9/1997 | Shorey et al. | 424/405 |
| 5,750,129 A | * | 5/1998 | Wakarachuk | 424/408 |

OTHER PUBLICATIONS

Qiu et al. "Pharmacokinetics, Formulation, and Safety of Insect Repellant N,N–Diethyl–3–Methylbenzamide (DEET):A Review" Journal of American Mosquito Control Association, Inc. 14(1) 12–27 (1998).*

Coats et al. "Toxicty and Neurotoxic Effects of Monoterpenoids" American Cancer Society (1991).*

Eisner, T. "Catnip: Its Raison d'Etre" Science, 146 1318–1320 (1964).*

Brief Reports "Terpenoids. Cis–trans and trans–cis Nepetalactones", Bates and Sigel.*

Adler, V.E., et al., "Evaluation of Selected Natural and Synthetic Products as House Fly Repellents", *J. Environ. Sci. Health*, 667–673, (1982).

Aldrich, J.R., et al., "Male–Specific Volatiles from Nearctic and Australasian True Bugs (Heteroptera: Coreidae and Alydidae)", 2767–2781, (1993).

Aldrich, J.R., et al., "Natural Products of Abdominal and Metathoracic Scent Glands of Coreoid Bugs", *Annals of the Entomological Society of America*, 68, 955–960, (Nov. 1975).

(List continued on next page.)

Primary Examiner—Jose' G. Dees
Assistant Examiner—Robert DeWitty
(74) Attorney, Agent, or Firm—Schwegman, Lundberg, Woessner & Kluth, P.A.

(57) ABSTRACT

This invention provides compositions and methods useful for repelling target pests. The compositions comprise an amount of a monoterpenoid or sesquiterpenoid effective to repel a target pest from a target area, the monoterpenoid or sesquiterpenoid in combination with a carrier. In one embodiment, the monoterpenoid or sesquiterpenoid is from a biorational source, such as a plant volatile. In a particular embodiment, the plant volatile is a monoterpenoid, such as "nepetalactone" (or the individual nepetalactone isomers) derived from catnip (*Nepeta cataria*). In another embodiment, the plant volatile is any one or a combination of sesquiterpenoids derived from the fruit of the Osage orange tree (*Maclura pomifera*). Such compositions have repellency against arthropods, such as cockroaches, mosquitoes, mites, ticks, spiders, and so forth.

10 Claims, 7 Drawing Sheets

OTHER PUBLICATIONS

Appel, A.G., et al., "Repellency of Milled Aromatic Eastern Red Cedar to Domiciliary Cockroaches (Dictyopter: Blattellidae and Blattidae)", *Entomological Society of America*, 82, 152–155, (Feb. 1989).

Baker, J.T., et al., "The Volatile Constituents of the Scent Gland Reservoir of the Fruit–Spotting Bug, Amblypelta Nitida", *Aust. J. Chem.*, 25, 393–400, (1972).

Bates, R.B., et al., "Terpenoids. Cis–trans– and trans–cis– Nepetalactones", *Breves comunications—Kurze Mitteilungen—Brevi communicazioni—Brief Reports*, 564–565, (1963).

Beavers, J.B., et al., "Synthetic Attractants for Some Dipteran Species", *Journal of Economic Entomology*, 65, 1740–1741, (Dec. 1972).

Bodenstein, O.F., et al., "Laboratory Evaluations of Compounds as Repellents to Cockroaches, 1953–1974", *United States Department of Agriculture*, Production Research Report No. 164, Biological Evaluation of Chemicals Laboratory, Northeastern Region, Agricultural Research Service, 1–28, (1976).

Burden, G.S., "Repellancy of Selected Insecticides", *Pest Control*, 16–18, (1975).

Carle, S.A., et al., "Variation in Host Fruit Volatiles Attractive to Apple Maggot Fly, Rhagoletis Pomonella", Department of Entomology, New York State Agricultural Experiment Station, Geneva, New York 14456, 795–805, (1987).

Charles, D.J., et al., "Essential Oil Constituents of Ocimum Micranthum Willd", *J. Agric. Food Chem.*, 38, 120–122, (1990).

Coats, J.R., et al., "Toxicity and Neurotoxic Effects of Monoterpenoids in Insects and Earthworms", *Naturally Occurring Pest Bioregulators*, Chapter 20, ACS Symposium Series: 449, pp. 305–316, (1991).

Deb–Kirtaniya, S., et al., "Extracts of Garlic as Possible Source of Insecticides", *Indian J. Agric. Sci.*, 50, 507–510, (Jun. 1980).

Edwards, D.L., et al., "Insect–Repellent–Induced Toxic Encephalopathy in a Child", *Clinical Pharmacy*, 6, 496–498, (Jun. 1987).

Eisner, T., "Catnip: Its Raison d'Etre", *Science*, 146, 1318–1320, (Dec. 1964).

Hernandez, M.M., et al., "Electroantennogram Activity from Antennae of Ceratitis Capitata (Wied.) to Fresh Orange Airborne Volatiles", *Journal of Chemical Ecology*, 22, 1607–1619, (1996).

Inazuka, S., "Monoterpenoids as Repellents against the German Cockroach (*Blattella Germanica* L.)", *Journal of Pesticide Science*, 8, 293–299, (Aug. 1983).

Inazuka, S., "New Methods of Evaluation for Cockroach Repellents and Repellency of Essential Oils against German Cockroach (*Blattella Germanica* L.)", *Journal of Pesticide Science*, 7, 133–143, (May 1982).

Karr, L.L., et al., "German Cockroach; Blattella Germanica (L.)", *Insecticide & Acaricide Tests*, 17, Laboratory Bioassay, Department of Entomology, Iowa State University, Ames IA, 393, (1991).

Karr, L.L., et al., "Insecticidal Properties of d–Limonene", *J. Pesticide Sci.*, 13, pp. 287–290, (1988).

Kaul, V.K., et al., "Essential Oil Composition of Bothriochloa Pertusa and Phyletic Relationship in Aromatic Grasses", *Biochemical Systematics and Ecology*, 26, 347–356, (1998).

Leach, G.J., et al., "Some Cardiovascular Effects of the Insect Repellent N,N–Diethyl–m–Toluamide (DEET)", *Journal of Toxicology and Environmental Health*, 25, 217–225, (1988).

Lewis, D.J., et al., "Evaluation of an Electronic Mosquito Repeller", *The Canadian Entomologist*, 114, 699–702, (Aug. 1982).

Mattheis, J.P., et al., "Identification of Headspace Volatile Compounds from 'Bing' Sweet Cherry Fruit", *Phytochemistry*, 31, 775–777, (1992).

Mauer, D.J., et al., "Attraction of Culex Pipiens Pipiens (Diptera: Culicidae) to Flower Volatiles", *Journal of Medical Entomology*, 36, 503–507, (Jul. 1999).

McElvain, S.M., et al., "The Constituents of the Volatile Oil of Catnip. I. Nepetalic Acid, Nepetalactone and Related Compounds", Contribution from the Laboratory of Organic of the University of Wisconsin, 1558–1563, (Jun. 1941).

Miller, J.D., "Anaphylaxis Associated with Insect Repellent", *The New England Journal of Medicine*, 1341–1342, (1982).

Ndungu, M., et al., "Cleome Monophylla Essential Oil and its Constituents as Tick (*Rhipicephalus Appendiculatus*) and Maize Weevil (*Sitophilus Zeamais*) Repellents", *Entomologia Experimentalis et Applicata*, 76, 217–222, (1995).

Porter, N.G., et al., "Chemical, Physical and Antimicrobial Properties of Essential Oils of *Leptospermum Scoparium* and *Kunzea Ericoides*", *Phytochemistry*, 50, 407–415, (Jun. 30, 1998).

Qiu, H., et al., "Pharmacokinetics, Formulation, and Safety of Insect Repellent N,N–Diethyl–3–Methylbenzamide (Deet): A Review", *Journal of the American Mosquito Control Association*, 14, 12–27, (Mar. 1998).

Regnier, F.E., et al., "The Biosynthesis of Methylcyclopentane Monoterpenoids–II", *Phytochemistry*, 7, 221–230, (1968).

Robbins, P.J., et al., "Review of the Biodistribution and Toxicity of the Insect Repellent N,N–Diethyl–m–Toluamide (DEET)", *Journal of Toxicology and Environmental Health*, 18, 503–525, (1986).

Rowley, W.A., et al., "A Microcomputer–Monitored Mosquito Flight Activity System", *Annals of the Entomological Society of America*, 80, 534–538, (Jul. 1987).

Sakan, T., et al., "The Synthesis of dl–Nepetalactone", *Short Communications*, 33, 1737–1738, (Dec. 1960).

Sakho, M., et al., "Enzymatic Maceration: Effects on Volatile Components of Mango Pulp", *Journal of Food Science*, 63, 975–978, (1998).

Sakuma, M., et al., "The Linear Track Olfactometer: An Assay Device for Taxes of the German Cockroach, *Blattella germanica* (L.) (Dictyoptera : Blattellidae) toward their Aggregation Pheromone", *Appl. Ent. Zool*, 20, Pesticide Research Institute, Kyota University, Kitashirakawa, Sakyo–ku, Kyoto 606, Japan, 387–401, (1985).

Scheffler, I., et al., "Behavioural Responses of German Cockroaches (*Blattella germanica* L.) Induced by Plant Repellents", In: *Insecticides: Mechanism of Action and Resistance*, D. Otto and B. Weber, ed., Intercept Ltd, Andover, England, 107–116, (1992).

Singh, D., et al., "Repellent and Insecticidal Properties of Essential Oils Against Housefly, *Musca Domestica* L", *Insect Sci. Applic.*, 12, 487–491, (1991).

Smith, R.M., et al., "Iridodials and Nepetalactone in the Defensive Secretion of the Coconut Stick Insects, *Graeffea Crouani*", *Journal of Chemical Ecology*, 5, 727–735, (1979).

Snook, M.E., et al., "Caffeoyltartronic Acid from Catnip (*Nepeta Cataria*): A Precursor for Catechol in Lubber Grosshopper (*Romalea Guttata*) Defensive Secretions", *Journal of Chemical Ecology*, 19, 1957–1966, (1993).

Snyder, J.W., et al., "Acute Manic Psychosis Following the Dermal Application of N,N–Diethyl–M–Toluamide (DEET) in an Adult", *Clinical Toxicology*, 24, 429–439, (1986).

Steltenkamp, R.J., et al., "Alkyl and Aryl Neoalkanamides: Highly Effective Insect Repellents", *Journal of Medical Entomology*, 29, 141–149, (Mar. 1992).

Sugawara, R., et al., "Attraction of Several Dipterous Insects to Aliphatic Esters (Diptera : Milichiidae, Chloropidae and Ceratopogonidae)", *Appl. Ent. Zool,* 9, Laboratory of Pesticide Chemistry, Faculty of Agriculture, Tokyo University of Education, Meguroku, Tokyo, 153 Japan, 11–18, (1974).

Sugawara, R., et al., "Attraction of the German Cockroach to Cyclohexyl Alkanoates and n–Aklyl Cyclohexaneacetates", *J. Insect Physiol,* 21, 957–964, (1975).

Watanabe, K., et al., "New Mosquito Repellent from *Eucalyptus Camaldulensis*", *J. Agric. Food Chem.,* 41, 2164–2166, (1993).

Williams, R.N., et al., "Rose Chafer (Coleoptera: Scarabaeidae): Improved Attractants for Adults", *Journal of Economic Entomology,* 83, 111–116, (Feb. 1990).

* cited by examiner

BIORATIONAL REPELLENTS OBTAINED FROM TERPENOIDS FOR USE AGAINST ARTHROPODS This application claims the benefit under 35 U.S.C. 119(e) of U.S. Provisional Application Serial No. 60/147,679 filed on Aug. 6, 1999, hereby incorporated by reference in its entirety. This application also claims the benefit under 35 U.S.C. 119(e) of U.S. Provisional Application Serial No. 60/150,051 filed on Aug. 20, 1999, hereby incorporated by reference in its entirety.

STATEMENT OF GOVERNMENT RIGHTS

This invention was made with Government support under United States Department of Agriculture Hatch funds (IAHEES), contract number IOW03187. The United States Government has certain rights in this invention.

FIELD

This invention relates to terpenoids and more particularly to monoterpenoids and sesquiterpenoids from biorational sources for use as repellents against arthropods.

BACKGROUND

The use of insect repellents is widely accepted throughout the world. Besides repellents intended for outdoor use, repellents are also available for use in homes to repel pests such as cockroaches, termites, ants, fleas, and so forth. The commercial standard for insect repellency is N,N-diethyl-3-methylbenzamide (DEET). The U.S. Environmental Protection Agency (EPA) estimates that more than 38% of the U.S. population uses a DEET-based insect repellent every year and that worldwide use exceeds 200,000,000 people annually (U.S. Environmental Protection Agency, PBS1-207722, 1980). However, DEET is known to cause severe adverse health effects in some people, particularly in higher concentrations. (See, for example, Qui et. al., 1998, *J. Am. Mosq. Control Assoc.* 14 (1):12–27; Miller, J. D., 1982, *New Eng. J. Med.* 307:1341–1342; Roland, et. al., 1985, *Can. J. Med. Assn. J.* 132:155–156).

Citronella is a biorational repellent that is also widely used. Although citronella poses less health risks than other, more toxic repellents, citronella is known to be highly volatile. As a result, any activity that might be present is lost rather quickly. In particular, citronella candles have been shown to be marginally effective, if at all.

Very little is known about the mechanisms involved in repelling many target pests such as cockroaches. It is also not known whether there are inherent differences between the ability of a male to detect a repellent as compared with a female of the same species.

What is needed, therefore, are new types of effective biorational repellents to replace commercial products that are toxic. The replacement repellents need to be economical, highly repellent to target pests, and pose less actual risk to the environment and humans as compared to traditional repellents.

SUMMARY

A repellent composition comprising an amount of a monoterpenoid or sesquiterpenoid effective to repel a target pest from a target area, the monoterpenoid or sesquiterpenoid in combination with a carrier is disclosed. In one embodiment, the monoterpenoid or sesquiterpenoid is from a biorational source, such as a plant volatile. In a particular embodiment, the plant volatile is a monoterpenoid, such as "nepetalactone" (or the individual nepetalactone isomers) derived from catnip (*Nepeta cataria*). In another embodiment, the plant volatile is any one or a combination of sesquiterpenoids derived from the fruit of the Osage orange tree (*Maclura pomifera*). Such compositions have repellency against arthropods, such as cockroaches, mosquitoes, mites, ticks, spiders, and so forth.

A method of repelling a target pest from a target area comprises applying an effective amount of a composition comprising the compound together with a suitable carrier in or near a target area, including applying the composition directly onto humans, animals (e.g., pets, livestock), and so forth. Repellents can also be applied to other target areas, including, but not limited to, plants, articles of clothing, tents, sleeping bags, pillows, bed nets, blankets, premises, etc.

It has also been determined that the chemoreceptors responsible for repellent response are present on the antennae of the German cockroach. Such chemoreceptors are likely present on the antennae of other arthropods as well. It has also been determined that male cockroaches are generally more sensitive to odors than female cockroaches.

DETAILED DESCRIPTION

Figure 1:
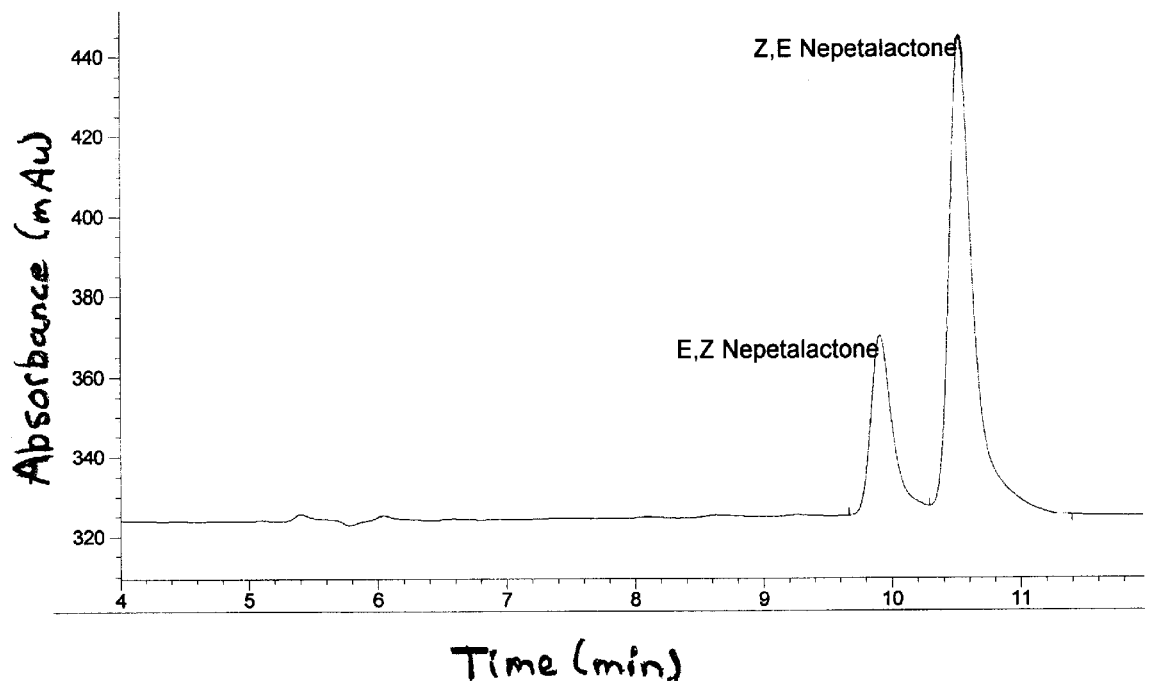
FIG. 1 shows a high performance liquid chromatograph ("HPLC") profile for the essential oil contained in a steam distillate of catnip in "absorbance" in milli-absorbance units (mAu) versus "time" in minutes (min), at a wavelength of approximately 254 nanometers (nm).

Compositions useful in repellency against arthropods are disclosed. Various terms are defined first, followed by a description of the preferred sources of the monoterpenoids and sesquiterpenoids, namely catnip and the Osage orange, respectively. The isolation methods and repellency of the various compositions made from these compounds is described next, followed by specific examples.

The term "applying" as used herein includes any suitable method of emitting an effective repellent amount of a plant volatile compound in a target area. This includes broadcast or restricted localized spraying of a volatile, in or around an area, with or without first micro-encapsulating the volatile, emitting the volatile from one or more controlled-release point-source dispensers in or around an area, and integrating the release of the volatile with an irrigation technique (chemigation). "Applying" can also refer to emitting liquid or solid repellents through use of creams, liquid-based products, powders, and so forth.

The term "biorational" as used herein refers to a pest management agent that is natural or otherwise based on biological approaches, such as plant products, insect hormones, pheromones, and so forth, as opposed to synthetic chemicals not based on any biologically-known compounds, e.g., DEET.

The term "carrier" as used herein refers to a component that, when combined with a repellent compound, produces a composition that can be delivered to a target pest as a repellent. A carrier can include, but is not limited to various liquids, solids and gases. This includes, but is not limited to, oils, including any type of vegetable oils, such as canola oil, soybean oil, and so forth, polymers, such as slow-release polymers, plastics, waxes, wood, gels, colloids, granular materials, such as clays and minerals (e.g., vermiculite, bentonite), dusts, powders, sprays, drenching means, emulsifiable concentrates, and so forth. This can include products such as floor polish, silicone caulking, as well as misters or aerosol sprays, and so forth. The choice of carrier depends on several factors, including, but not limited to, the specific need, the size of the target area, and so forth.

As used herein, the term "controlled-release point-source dispenser" is one type of delivery means for a composition comprising the repellent compound and a carrier. Such a dispenser includes any suitable method for controlling the emission rate of the volatile compound from a concentrated source reservoir of the compounds. Such methods include, but are not limited to, pads, beads, rods, spirals, or balls comprised of rubber, leather, cotton, wood or wood products, polyethylene, polypropylene or polyvinyl chloride that are impregnated with the volatile compound; micro-capillary tubes open at one end; sealed polyethylene or polypropylene tubes sealed at both ends; laminates comprised of layers of the volatile compound alternated with plastic and cut in various sized flakes or preserved as large ribbons or sheets; permeable or semi-permeable membranes covering a non-permeable container serving as a reservoir for the volatile compounds; large porous beads or sponges; micro-capsules; sealed envelopes or bags made of polyethylene, polypropylene, paper, cardboard, or other permeable substances, metered aerosol systems utilizing pump or pressure technologies to emit aerosolized droplets of the volatiles into the atmosphere, onto plants surfaces or soil, or onto any of the above controlled-release point-source dispensers; and non-aerosol micro-pump technologies that cause metered quantities of the compounds to be dispensed and volatilized by any of the above methods.

The term "essential" as used herein in the phrase "essential oil" refers to the "essence" or "smell" of the oil that is distinctive to a particular plant, such as catnip or Osage orange. The "essential oil" of a plant contains the volatile components.

The term "fumigation" as used herein refers to the use of a gas repellent, or a volatile solid or liquid repellent to control pests in storage bins, buildings, ships, rail cars, stored products, organic materials such as soil, foods, animal feed, compost, and so forth, living organisms such as plants, or in any closed areas, i.e., target areas, which are prone to having pests, i.e., pest infestation.

The term "mature" or "ripe" as used herein typically refers to a fruit that has detached from a branch and fallen to the ground, although a "ripe" fruit in some instances may still be attached to the branch and within a few days of detaching. An "unripe" or "immature" fruit is necessarily a fruit that is still attached to a branch, but is not within a few days of detaching from the branch. In some instances, "maturity" can be defined by the calendar, such that fruit collected after a certain date is considered "ripe," whereas fruit collected prior to that date is typically "unripe." For example, fruit of the Osage orange which is collected after approximately September 30 in the Northern Hemisphere is generally considered to be "ripe," whereas fruit collected prior to that date in this hemisphere is typically in an "unripe" state. Obviously, the growing season can vary from year to year and at different latitudes. For example, in some years "ripe" Osage orange fruit may be present as early as mid-September, whereas, "unripe" Osage orange fruit may still be present in mid-October. With respect to many fruits, such as the Osage orange, it appears that the chemical make-up is different in a "ripe" fruit as compared with an "unripe" fruit. For example, preliminary tests indicate that "ripe" Osage oranges have a significant amount of hexyl hexanoate, i.e., in excess of about 30% of the volatile fraction whereas "unripe" fruit does not appear to have more than trace amounts of this compound.

The term "monoterpene" as used herein refers to a compound having a 10-carbon skeleton with non-linear branches. A monoterpene technically refers to a compound with two isoprene units connected in a head-to-end manner. The term "monoterpenoid" refers to a monoterpene-like substance and may be used loosely herein to refer collectively to monoterpenoid derivatives as well as monoterpenoid analogs. Monoterpenoids can therefore include monoterpenes, alcohols, ketones, aldehydes, esters, ethers, acids, hydrocarbons without an oxygen functional group, and so forth. It is common practice to refer to certain phenolic compounds, such as eugenol, thymol and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein.

As used herein, the term "repel" means that less time is spent in a given area, i.e., a target area, than in an available non-target or untreated area. "Repel" can also mean that no time is spent in the target area. As such, "repelling" a pest includes deterring a pest from remaining in a target area, as well as keeping a pest away from a target area. In some instances, "repel" may include killing a target pest. In some instances, a pest may be "slowed" in behavior and responsiveness after coming in contact with a repellent, such that the presence of the target pest is less of a nuisance to a human or animal in the target area. Slowing a target pest may also allow it to be killed by other means. The total number of pests in an area may be considered to be "suppressed" or even "eliminated" due to use of a "repelling agent" or a "repellent."

The term "sesquiterpene" as used herein refers to a compound having a 15-carbon skeleton with non-linear branches. The term "sesquiterpenoid" refers to a sesquiterpene-like substance and may be used loosely herein to refer collectively to sesquiterpenoid derivatives as well as sesquiterpenoid analogs. Sesquiterpenoids can include sesquiterpenes, alcohols, ketones, aldehydes, ethers, acids, hydrocarbons without an oxygen functional group, and so forth.

The term "suppress" as used herein means to reduce or limit the incidence or severity of a pest infestation or pest activity, even if for a limited period of time.

The term "target area" as used herein includes any place where the presence of target pests is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth. Target area can also include the outer covering of a living being, such as skin, fur, hair, or clothing.

The term "volatility" as used herein is defined as the property of a substance having a low boiling point and a high vapor pressure at ordinary temperatures and pressures. Similarly, the term "volatile" is considered to refer to a compound that is readily vaporizable at a relatively low temperature. A "slightly volatile" compound may be considered to have a vapor pressure of between about 0.05 Pascal (Pa) and two (2) Pa. Slightly volatile repellents can be considered to include DEET (vapor pressure of 0.22 Pa), as well as many of the preferred repellents of the present invention that contain nepetalactone, nepetalactone isomers or certain sesquiterpenoids. "Slight" volatility is a desirable property for a repellent because it provides an additional route of exposure against a target pest, i.e., fumigation. Furthermore, the same amount of such a repellent is effective over a larger target area as compared with a non-volatile repellent, which is limited to only a contact route of exposure. "High" volatility is generally considered an undesirable property for a repellent, because such repellents typically dissipate too rapidly to be effective, e.g., citronella. The essential oil of a plant is considered to include only "volatile" components. Similarly, the term "plant volatile" as used herein refers to a volatilizing compound from any part of a plant, including, but not limited to, a leaf, root, flower or flower bud, fruit, vegetable, stem, and so forth.

The compounds useful in the present invention are volatile terpenoids. The preferred compounds are slightly volatile compounds from plant volatiles and include monoterpenoids and sesquiterpenoids. Specific preferred compounds are the monoterpenoids nepetalactone, including two of the individual isomers of nepetalactone, namely the Z,E- and E,Z-isomers. Other specific preferred compounds include hedycaryol, elemene, elemol, alpha-cubebene, cadinene, as well as other sesquiterpenoids listed in Tables 5–7.

These compounds, when combined with a suitable carrier or vehicle, can be used as an insect repellent in target areas that include people, pets, livestock, cupboards, containers, houses, yards, gardens and so forth. The repellents can be used against a variety of target pests including cockroaches, mosquitoes, black flies, house flies, gnats, stored grain pests (e.g., maize weevil, red flour beetle, saw-toothed grain beetle, Indian meal moth), clothes moths, ticks, mites, spiders, and other arthropod pests.

Various terpenoid compounds are isolated and purified from any source by any suitable method. In one embodiment, biorational sources, such as plants, fruits, and so forth, are used. In a particular embodiment, catnip (*Nepeta cataria*) is used as the source of nepetalactone, although the invention is not so limited. Nepetalactone is chemically related to certain cyclopentanoid monoterpenes isolated from insects, many of which are components of defensive secretions. (Eisner, T., 1964, *Science*. 146:1318). In a particular embodiment, two of the isomers of nepetalactone, namely cis-trans nepetalactone ("Z,E-isomer" or "Z,E-nepetalactone") and trans-cis nepetalactone ("E,Z-isomer or "E,Z-nepetalactone"), can each be used individually as the active compound in a repellent composition. In one embodiment, these isomers are also isolated and purified from the essential oil of catnip which is known to contain the monoterpene-derived iridodial compound nepetalactone (5,6,7,7a-tetrahydro-4,7-dimethylcyclopenta[e]pyran-1-(4H)-one) (McElvain et al, 1941, *J. Am. Chem. Soc*. 63:1558–1563). It may be that these and other isomers, such as the Z,Z-isomer or E,E-isomer may be derived from other plants sources, such as *Nepeta mussini, Nepeta grandiflora* and *Nepeta nuda*. Such plant sources may also be used as an alternate source for nepetalactone. (See Eisenbraun, et al., 1980, *J. Am. Chem. Soc*. 45, 3811–3814).

Sesquiterpenoids are also useful as repellents and can be found in any number of biorational sources. In one embodiment, the fruit of the Osage orange tree (sometimes referred to as "hedge apple") is used as the source of the sesquiterpenoids. Other sources include, for example, *Ocimum micranthum* (Peruvian basil), which is known to contain γ-elemene isomers, β-elemene isomers, γ-copaene and β-selinene (Charles et al., 1990, J. Agric. Food Chem. 38(1): 120–122). The aromatic grass *Bothriochloa pertusa* is known to contain α-selinene, τ-cadinene, δ-cadinene and elemol (Kaul and Vats, 1998, Biochem. Syst. Ecol. 26: 347–356). Mangoes contain δ-cubebene, β-elemene, δ-selinene and γ-cadinene following enzymatic maceration (Sakho et al., 1998, J. Food Sci. 63(6): 975–978). Several compounds have been isolated from navel oranges, including β-copaene, δ-cadinene and hexyl hexanoate. Cubebene has been identified as a minor component of the shrub *Cleome monophylla* extracts. Sesquiterpenoids possessing the cubebene/copaene, elemene, selinene and cadinene skeletons were identified from antimicrobial extracts of *Leptospermum scoparium* and *Kunzea ericoides* (Porter and Wilkins, 1998, Photochemistry 50: 407–415).

The isolated terpenoid can be of any suitable purity, such as 55% or more. In one embodiment, the purity is at least about 90%. In another embodiment, the purity is greater than 90%. In yet another embodiment, the purity is in excess of 99%.

Different formulations or routes of exposure can provide for even further uses. For example, in addition to exposing the target pest to the repellent by contact, and possibly aquatic exposure, any of these novel repellents can also be used as fumigants. Useful amounts to evoke repellency ("repellent" amounts) will depend on the particular application technique used and on the specific conditions in the area at the time of application. Such amounts can readily be determined by those skilled in the art. The determination by Applicants of the means of sensory input for the German cockroach, and likely other target pests as well, i.e., via antennae, will also aid in determining proper amounts for various applications.

In this study, nepetalactone was isolated from catnip by subjecting the leaves and stems to steam distillation. Nepetalactone purity in excess of 99% was achieved with this method. The resulting extract was tested for repellency against male German cockroaches (*Blattella germanica*) in a "choice" test arena, i.e., via contact. The two isomers of nepetalactone were also isolated, purified by preparative thin-layer chromatography (TLC), and tested for repellency in the same manner. Purity in excess of 97% was achieved for the Z,E-isomer and in excess of 91% for E,Z-isomer. (Nuclear magnetic resonance (NMR) testing can also be used for additional verification with isomers having even higher purity, i.e., about 99% or more). The nepetalactone isomers have the following structures:

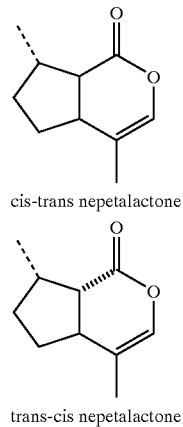

cis-trans nepetalactone trans-cis nepetalactone

Significant differences due to concentration were detected using Analysis of Variance (ANOVA), a statistical method known in the art for finding significant differences between treatment types by analyzing variance between observations. Responses were compared using the well-known least-squared means analysis method. The minor isomer, E,Z-nepetalactone, appears to be significantly more repellent than the predominant isomer, Z,E-nepetalactone. Furthermore, at the lowest concentrations tested, the E,Z-isomer appears to be far more repellent to cockroaches than DEET, the primary known commercial standard insect repellent. It should be noted that known cockroach "insecticides" include various organophosphates, carbamates and pyrethroids. However, DEET and naphthalene have been used herein as the standards for comparison against the cockroach because there is no known cockroach "repellent" commercially available. (See Example 1).

The mature and immature fruits of the Osage orange (*Maclura pomifera*, family Moraceae) were extracted using several methods, including steam distillation, solid-phase micro-extraction (SPME), solvent extraction with hexane and Soxhlet extraction with hexane or methylene chloride. Each of these techniques resulted in an essential oil containing a number of sesquiterpenoids and other components. The extracts were subjected to gas chromatography and mass spectroscopy (GC-MS) to identify extract components. Ripe and unripe fruits were also compared using solid-phase micro-extraction (SPME). In addition to testing the essential oil of the Osage orange against the cockroach in a "choice" test arena, three of the identified components in the essential oil have also been similarly tested for repellency, namely elemol, alpha-cubebene and hexyl hexanoate (a non-sesquiterpenoid). Two other identified non-sesquiterpenoids that are not in the essential oil have also been tested, namely, osajin and pomiferin.

Results to date indicate that the sesquiterpenoid components in the Osage orange have excellent repellency against pests as compared with the non-sesquiterpenoids. Osajin, a non-sesquiterpenoid, did demonstrate repellency, but since it has no volatility, it can only be used as a contact repellent. The sesquiterpenoids also appear to have better efficacy than naphthalene, another commercial standard insect repellent (commonly used in moth balls). It is believed that several of the other sesquiterpenoids present in the essential oil (or combinations thereof) will also demonstrate similar or perhaps even better repellency properties. (See Example 2).

An experiment was also conducted to determine how arthropods detect repellents. It is known that DEET is effective as a repellent against mosquitoes because it can mask the odor of lactic acid, likely by interacting with a lactic acid receptor in the antennae of the mosquito. (E. Davis et al., 1976, *J. Comp. Physiol.* 150, 43–54). However, it is not known how other repellents are detected by mosquitoes, nor is it known how pests other than mosquitoes detect any type of repellent. In order to determine whether the antenna plays a role in repellent detection for arthropods other than mosquitoes, the experiment involved removing the antennae of several German cockroaches. The antennectomized cockroaches were exposed to concentrations of repellents that were shown to be active in the previous experiment. In all cases, the cockroaches were indifferent to the repellents, spending a nearly equal time on each piece of filter paper, i.e., treated and untreated. Since these cockroaches had never before encountered these repellents, the response was not considered to be learned or conditioned behavior. This experiment conclusively demonstrates that cockroaches, and likely most other arthropods having antennae, detect repellents with their antennae. (See Example 3).

Differences between male and female cockroaches were also evaluated. It was confirmed that male cockroaches are more sensitive to odors than females. Female cockroaches were indifferent to DEET at concentrations that produced a definitive response in males. The females were also less strongly repelled by the Osage orange extract than the males. (See Example 4).

Preliminary tests with two species of mosquito, namely *Aedes aegypti* and *Culex tarsalis*, determined lethal levels of both the monoterpenoid and sesquiterpenoid compositions. (Example 5). Additional tests will likely show that these compounds are repellent against these insects as well. (See Examples 6–7).

The invention will now be illustrated by the following non-limiting Examples.

EXAMPLE 1

Materials and Methods

Insects. German cockroaches (*Blattella germanica*) were obtained from a colony at the Entomology Department of Iowa State University, Ames, Iowa. This colony was established several years ago by trapping wild cockroaches. The cockroaches have been kept in a 20-gal fish aquarium having approximately the top five (5) cm lined with "Insect Trap Coating" made by the Tanglefoot Company in Grand Rapids, Mich. The next five (5) cm is lined with conventional petroleum jelly to help prevent the cockroaches from entering the coating, where they will die. The aquarium is covered with a piece of plexiglass having about a 7.5 cm (three (3) in) hole into which a screen has been placed. Small cardboard shelters are also kept in the aquarium to provide a place for the cockroaches to hide. A water bottle stopped with a dental wick is kept in the aquarium along with any conventional type of dry cat food in the cage bottom. Typically about ½ cup of dry cat food is kept in the cage. The cockroaches present in the aquarium are typically a combination of recently-trapped cockroaches and the existing colony of cockroaches. Additional cat food, such as about ¼ cup once a week, is added to the aquarium. Old cat food is removed and replaced periodically, particularly if it develops mold. Fresh water is also added to the water bottle periodically. The water bottle is replaced if mold develops on the wick. Approximately every four (4) to six (6) months, the colony is transferred to a clean aquarium.

Standard and Comparison Compounds. DEET was purchased from Aldrich Chemicals in Milwaukee, Wis. Acetone and hexane, each having a purity in excess of 99% were purchased from Fischer Scientific Inc. in Pittsburgh, Pa.

Starting Materials. Fresh catnip at various flowering stages was collected from unsprayed wild areas of the Iowa State University campus in Ames, Iowa as needed during the growing season. Plants not distilled immediately were frozen at −80° C. until needed for steam distillation. In some instances, frozen plants were used in conjunction with fresh catnip. The leaves and stems were either crushed while still frozen or otherwise cut up into small pieces while still fresh, in preparation for steam distillation. The crushed or cut-up leaves and stems were then placed into a five (5)-liter three-necked boiling flask and steam distilled according to the method of Pavia, et al., 1988, *Introduction to Organic Laboratory Techniques,* 3rd edition, Harcourt Brace College Publishers, Fort Worth, Tex. The collected distillate was washed two times with one (1) volume each of hexane in a separatory funnel to remove the oil layer from the water layer. The hexane was removed using rotary evaporation vacuum distillation at 500 mm Hg vacuum and 25° C.

A portion of the liquid obtained from rotary evaporation was diluted to about one (1) μl/ml with hexane and subjected to chromatographic analysis. Identification of the components was obtained using a Varian Gas Chromatograph, series 3700, with a two-meter packed 3% OV 101 column, nitrogen carrier, FID-detector, injector temperature of 250° C., an injection volume of 1.5 μl, with an initial column temperature of 70° C., ramped at 5° C./min to 150° C. and held for 8 minutes. The Z,E-isomer had a retention time of about 10.75 min, and the E,Z-isomer had a retention time of about 11.25 min. The ratio of Z,E- isomer to E,Z-isomer was about 6:1, as determined by calculating the areas under the peaks. These isomers together comprised over 98% of the steam distillate. Minor components were not identified.

HPLC was conducted using a Hewlett Packard series 1100 HPLC with a Pirkle Covalent Phenylglycine hi-chrom preparative column (25 cm×10 mm I.D., 5 microns S5NH Modified Spherosorb), having an injection volume of 25 μl, a mobile phase of 9:1 hexane:ethyl acetate at about 2.5 ml/min flow rate, and detection using a Spectroflow 757 UV-Detector at 254 nm.

The two isomers of nepetalactone were separated using silica gel preparative TLC plates (Whatman 20×20 cm, thickness: 1000 μm) with a solvent system of approximately 19:1 hexane:ethyl ether. The plates were run seven (7) times, allowing them to dry completely between each run. The resulting bands, which included a "wide" band and a "thin" band, were each illuminated under 254 nm UV-light. The silica gel was then scraped off the plates and washed with three washings of ether. The resulting solution was filtered and the ether solvent was removed by rotary evaporation. Purity was assessed using HPLC.

Figure 2:
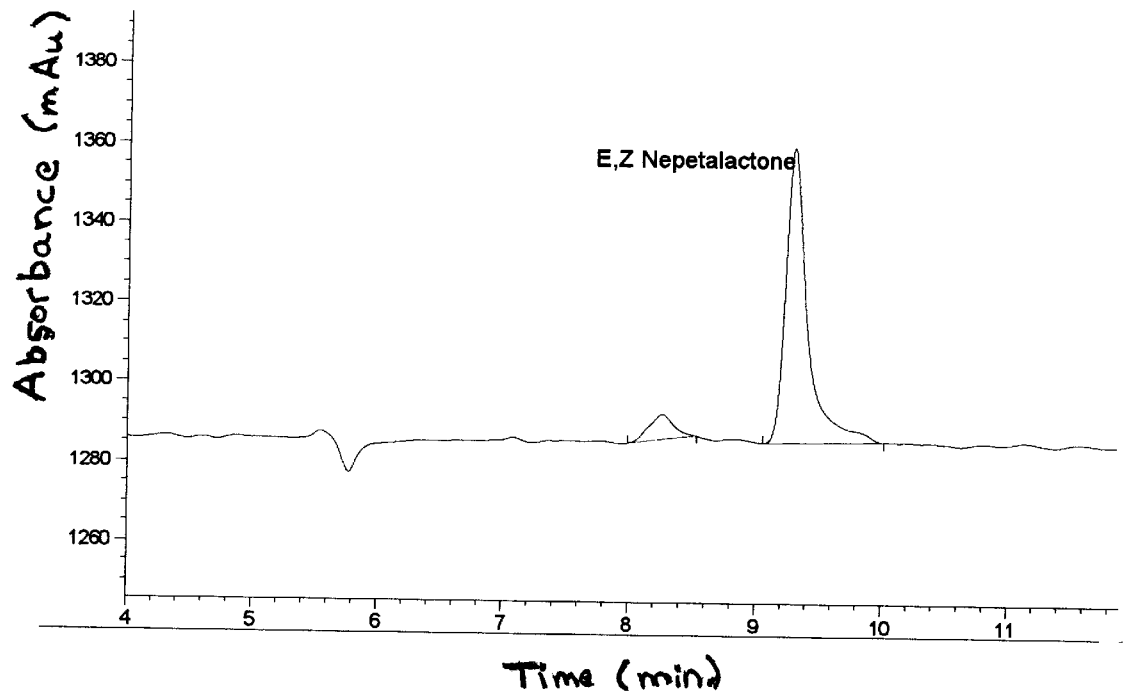
FIG. 2 shows an HPLC profile for E,Z-nepetalactone isolated from the steam distillate described in FIG. 1 in absorbance (mAu) versus time (min), at a wavelength of approximately 254 nanometers (nm).
Figure 3:
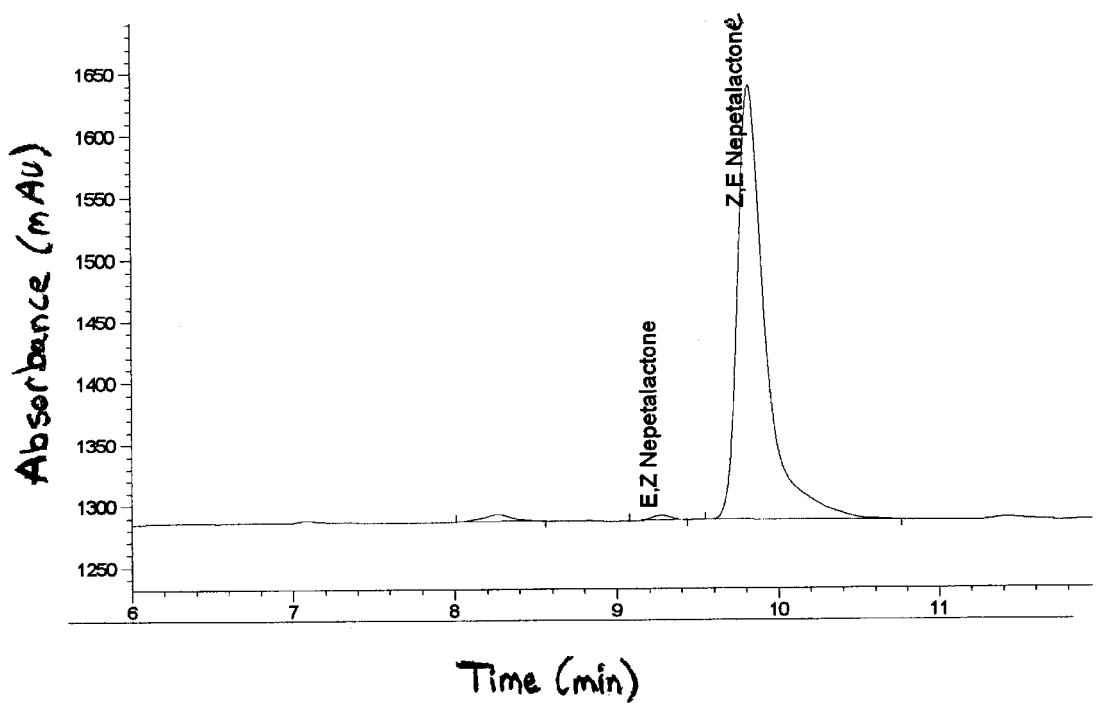
FIG. 3 shows an HPLC profile for Z,E-nepetalactone isolated from the steam distillate described in FIG. 1 in absorbance (mAu) versus time (min), at a wavelength of approximately 254 nanometers (nm).

Retention times and area percentage for the steam distillate and the two isomers are shown in Table 1 and FIGS. 1–3.

TABLE 1

HPLC Results for Catnip Steam Distillate, E,Z-Isomer and Z,E-Isomer

|  | E,Z-isomer | Z,E-isomer |
| --- | --- | --- |
| (FIG. 2) Catnip steam distillate retention time (minutes) | 9.9 | 10.5 |
| area % | 25.2 | 74.8 |
| (FIG. 3) "wide" band on TLC retention time (minutes) | — | 9.3 |
| area % | — | 91.3 |
| (FIG. 4) "thin" band on TLC retention time (minutes) | 9.8 | — |
| area % | 97.5 | — |

As Table 1 shows, the wide band on the TLC plate consisted predominantly of the Z,E-isomer, and the thin band was determined to consist mostly of the E,Z-isomer. On HPLC, as shown in FIG. 1, the second peak represents the Z,E-isomer, and the first peak is the E,Z-isomer. Comparing the areas for each band, the HPLC graphs show that the TLC procedure was accurate and efficient in separating the two isomers. FIG. 1 indicates a purity of the steam distillate in excess of about 99%, with about 25.2% of E,Z-isomer present and about 74.8% of the Z,E-isomer present. FIG. 2 indicates a purity of the E,Z-isomer of at least about 91.3%. The remaining components are unknown at this time. Similarly, FIG. 3 shows that the Z,E-isomer can be isolated at a purity of at least about 97.5%, with the remaining components being about 0.8% of the E,Z isomer and about 1.7% unknowns.

Gas-chromatography/mass spectroscopy of the nepetalactone isomers was also conducted on a Varian 3400 gas chromatograph, with a DB-5ms nonpolar 30-m column (0.25 mm ID, 0.25 mm film thickness). The gas chromatography was coupled to a Finnigan TSQ 700 triple quadrupole mass spectrometer (San Jose, Calif.), electron impact of 70 eV. The mass spectral analysis of the isomers revealed that the two compounds are nearly indistinguishable by mass spectrometry, as is expected with isomers. The Z,E-isomer eluted off the column at 2.26 minutes, showing ions at m/z 166 [M$^+$] (100%), m/z 123 (78.5%), m/z 109 (46.3%), m/z 95 (58.8%), m/z 81 (62.2%) and m/z 69 (46.7%). The E,Z-isomer eluted off the column at 2.67 with the following mass spectrum: m/z 166 [M$^+$] (100%), m/z 166 (99.9%), m/z 109 (51.8%), m/z 95 (66..6%), m/z 81 (67.0%) and m/z 69 (50.2%). Since both peaks have essentially identical mass spectra, these results are a further indication that the compound is nepetalactone, even though it contains two different isomers.

Test procedure. Repellency bioassays were conducted to assess the repellent properties of compositions containing catnip steam distillate (nepetalactone), Z,E-nepetalactone, E,Z-nepetalactone and DEET against cockroaches. Certified acetone and certified hexane were also tested in order to evaluate solvent effects. (DEET was dissolved in acetone, because DEET is insoluble in hexane. The tested compounds were dissolved in hexane because hexane was the solvent used to extract these compounds from the distillate).

One Whatman 125-mm round filter paper was cut in half. One side was treated with one (1) ml of the test compound and the other side was treated with one (1) ml of solvent. The papers were allowed to dry in a fume hood for approximately two (2) minutes before being placed in a 150-mm Petri dish arena. The relative position of the treated side (i.e., to the right or left) of the dish was randomized using a random number table. The top of the Petri dish had a hole cut into the center for introduction of one cockroach at a time directly into the center of the arena. The hole was stopped using a small piece of tape to prevent the insect from escaping. One adult male German cockroach (*Blattella gennanica*) was selected from the colony and dropped into the pre-formed hole in the Petri dish lid. Immediately after introduction of the cockroach, the number of seconds the cockroach spent on the treated or untreated side during a 300-second (five (5) minute) period was recorded with two different (2) stopwatches. Ten (10) replications were performed for each test compound.

Results and Discussion

Repellency bioassays. Using mean values and their related Standard Error of the Mean values (SEM), repellency of the selected samples was determined as shown in Table 2. Significance due to concentration was determined using ANOVA. Means for each dose were compared using the least squared means analysis on SAS (SAS Institute 1991) as shown in Table 3. Table 3 also shows a percent repellency for each test performed. Comparisons between test compounds were made using a two-tailed paired t-test ("paired t-test") which indicates "differences" as is known in the art and shown in Table 4 (as compared with a "one-tailed" test, which indicates "greater or less than").

TABLE 2

Nepetalactone and Nepetalactone Isomer Repellency Against the German Cockroach as Compared with DEET, Acetone and Hexane

| | | Results of 300-second tests | | | |
|---|---|---|---|---|---|
| Controls | Treated vs Untreated | Mean Treated (seconds) | SEM | Mean Untreated (seconds) | SEM |
| | Acetone vs Acetone | 143 | 11.2 | 159 | 11.3 |
| | Hexane vs Hexane | 147 | 5.6 | 155 | 5.5 |
| DEET | | | | | |
| | 10% vs Acetone | 63.4 | 15.9 | 238 | 15.6 |
| | 5% vs Acetone | 113 | 14.5 | 190 | 14.1 |
| | 1% vs Acetone | 120 | 13.8 | 181 | 13.8 |
| | 0.5% vs Acetone | 128 | 9.7 | 175 | 9.6 |
| | 0.1% vs Acetone | 129 | 9 | 175 | 8.8 |
| Nepetalactone Steam distillate | 5% vs Hexane | 68 | 14.7 | 235 | 14.7 |
| | 1% vs Hexane | 109 | 19.6 | 192 | 19.8 |
| | 0.5% vs Hexane | 105 | 23.6 | 206 | 24.5 |
| Z,E-isomer | | | | | |
| | 5% vs Hexane | 47.3 | 8.7 | 252 | 8.4 |
| | 1% vs Hexane | 65.4 | 11.8 | 236 | 11.5 |
| | 0.5% vs Hexane | 128 | 10.4 | 174 | 10.3 |
| | 0.1% vs Hexane | 127 | 11.2 | 176 | 11.2 |
| E,Z-isomer | | | | | |
| | 0.5% vs Hexane | 31.7 | 5.2 | 270 | 5.3 |
| | 0.1% vs Hexane | 76.7 | 13.7 | 216 | 20.2 |

As Table 2 shows, control bioassays involving acetone and hexane showed no significant repellency. DEET at a level of ten (10)%, by volume, in the test solution was highly repellent. However, when comparing five (5)% DEET to five (5)% catnip (by volume) steam distillate, it can be seen that the catnip essential oil was a more effective repellent (as determined by the difference between the two mean values). Additionally, the one (1)% catnip steam distillate repelled cockroaches better than one (1)% DEET. At the 0.5% and 0.1% concentration levels, the E,Z-isomer repelled significantly better than the extract, DEET, and the Z,E-isomer (in descending order of comparative repellency).

The mean number of seconds spent by the cockroaches on the treated side of the arena, plus or minus the standard error of the mean (SEM) is reported in Table 3. The amount of test compound per unit area of filter paper is noted in "$\mu g/cm^2$" in Table 3. The percent by weight of each component listed in Table 2 can be converted "$\mu g/cm^2$" by the following formula: ($\mu g$ of compound/one (1) ml of solution)/area of filter paper in $cm^2$. For example, a solution containing "five (5)%", by volume, of a compound, is equivalent to a concentration of approximately "800 $\mu g/cm^2$" of that compound (e.g., five (5)% DEET is equivalent to a concentration of about 800 $\mu g/cm^2$ of DEET). Similarly, one (1)% DEET is equivalent to a concentration of approximately 160 $\mu g/cm^2$.

TABLE 3

Mean number of seconds (±SEM) spent on the treated side of the test arena by male *R. germanica* in 300 seconds

| Test Solution | Dose ($\mu g/cm^2$) | Mean seconds on treated side ± SEM | % repellency * |
|---|---|---|---|
| DEET | 1600 | 63.4 ± 15.9 b | 58 |
| | 800 | 113 ± 14.5 a | 26 |
| | 160 | 120 ± 13.8 a | 20 |
| | 80 | 128 ± 9.7 a | 16 |
| | 16 | 129 ± 9.0 a | 15 |
| | 0 | 143 ± 11.2 a | 5 |
| Catnip Essential Oil | 800 | 68.3 ± 14.7 b | 56 |
| | 160 | 109 ± 19.6 ab | 28 |
| | 80 | 105 ± 23.6 ab | 34 |
| | 0 | 147 ± 5.6 a | 3 |
| Z,E-Nepetalactone | 800 | 47.3 ± 8.7 b | 68 |
| | 160 | 65.4 ± 11.8 b | 57 |
| | 80 | 128 ± 10.4 a | 15 |
| | 16 | 127 ± 11.2 a | 16 |
| | 0 | 147 ± 5.6 a | 3 |
| E,Z-Nepetalactone | 80 | 31.7 ± 5.2 c | 79 |
| | 16 | 76.7 ± 13.7 b | 46 |
| | 0 | 147 ± 5.6 a | 3 |

For each test solution, means ± SEM followed by the same letter are not significantly different by least squared means analysis ($\alpha = 0.05$).
*Percent repellency was calculated by the following formula: (untreated-treated/300)*100

Significance due to concentration was observed by two-tailed ANOVA for DEET (F=4.83, df=5, 54; P=0.001), Z,E-nepetalactone (F=20.00, df=4, 45; P=0.0001) and E,Z-nepetalactone (F=41.08, df=2,27; P=0.0001). Significance due to concentration was not seen for the catnip essential oil at the 0.05 two-tailed significance level, but was seen at the 0.1 significance level (F=3.44, df=3, 36; P=0.0267). As shown in Table 3, all DEET concentrations tested below 1600 $\mu g/cm^2$ were not significantly different from the control by least squared means analysis ($\alpha=0.05$). However, catnip essential oil was significantly different from the control at a dose of 800 $\mu g/cm^2$. Furthermore, Z,E-nepetalactone was significantly different from the control at doses of 160 $\mu g/cm^2$ and higher. E,Z-Nepetalactone was also significantly different from the control at all doses tested, including the lowest tested dose of approximately 16 $\mu g/cm^2$.

Paired t-test comparisons ($\alpha=0.05$. df=9) between the different compounds at equivalent doses were made and shown below in Table 4.

TABLE 4

Paired t-test comparisons of equivalent doses of test compounds

| Dose ($\mu g/cm^2$) | Comparison | vs. | Calculated t-value |
|---|---|---|---|
| 800 | DEET | CNEO | 2.29* |
|  | DEET | Z,E | 3.88* |
|  | CNEO | Z,E | 1.75 |
| 160 | DEET | CNEO | 0.41 |
|  | DEET | Z,E | 4.41* |
|  | CNEO | Z,E | 1.91 |
| 80 | DEET | CNEO | 0.88 |
|  | DEET | Z,E | 0.01 |
|  | DEET | E,Z | 7.82* |
|  | CNEO | Z,E | −0.88 |
|  | CNEO | E,Z | 2.99* |
|  | Z,E | E,Z | 7.87* |
| 16 | DEET | Z,E | 0.10 |
|  | DEET | E,Z | 2.60* |
|  | Z,E | E,Z | 2.50* |

*Difference is significant by two-tailed paired t-test at $\alpha = 0.05$, df = 9.
CNEO = Catnip essential oil; Z,E = Z,E-Nepetalactone; E,Z = E,Z-Nepetalactone.

As Table 4 shows, catnip essential oil only differed from DEET at 800 $\mu g/cm^2$, and not at lower doses. Z,E-Nepetalactone differed from equivalent doses of DEET above 80 $\mu g/cm^2$. However, E,Z-nepetalactone differed from DEET at all concentrations tested. Z,E-Nepetalactone, which comprises about 85% of the essential oil, did not differ from the catnip essential oil at any of the concentrations tested. E,Z-Nepetalactone was more active than the catnip essential oil at 80 $\mu g/cm^2$. Both Z,E- and E,Z-nepetalactone were compared at 80 and 16 $\mu g/cm^2$. It was found that E,Z-nepetalactone was significantly more active than the Z,E-isomer at both concentrations.

Conclusions

The crude steam distillate (nepetalactone) displayed "very good" repellency at every concentration tested, as is evidenced by the minimal amount of time the cockroach stayed on the treated side, as compared with the untreated side, i.e., approximately two (2) to three (3) times less. The individual isomers also demonstrated "very good" to "excellent" results. For example, the Z,E-isomer at five (5)% demonstrated "excellent" repellency, as the cockroach spent about five (5) times less time on the treated side as compared with the untreated side. The E,Z-isomer at 0.5% demonstrated "highly superior" repellency, as the cockroach spent about eight (8) times less time on the treated side as compared with the untreated side. It is quite likely that repellency would be high at other values as well. These compounds, in combination with a suitable carrier or delivery means have been demonstrated to be better than the commercial standard (DEET) for repellency against the German cockroach. Likely these compounds are also repellent against other arthropods as well.

EXAMPLE 2

Insects. Cockroaches from the same source as described in Example 1 were used.

Standards and controls. Naphthalene having a purity in excess of 99% was obtained from Fischer Scientific Inc. The naphthalene, which was dissolved in acetone prior to testing, was used as a standard as this is one of the components in moth balls, a product used to repel clothes moths. (Again, there is no commercial standard for cockroach "repellents" per se, only for cockroach "insecticides"). Hexane having a purity in excess of 99% was also obtained from Fischer Scientific Inc.

Starting Materials. A series of GC-MS tests was undertaken to determine the various components of the Osage orange that could potentially be used as starting materials for repellency testing. The components were isolated using the methods described below, including steam distillation, Soxhlet extractions and hexane soaking (see Tables 5–6), as well as solid-phase micro-extractions (SPME) (see Table 7).

Some of the identified components were purified to at least about 95% and used in the repellency studies. Other identified components were purchased for use in these studies. All of these components were then dissolved in solvents prior to repellency testing. Specifically, osajin and pomiferin were purified to approximately 95% and 98%, respectively, and dissolved in acetone. Hexyl hexanoate and alpha-cubebene, having purities of 97% and 98%, respectively, were purchased from Fischer Scientific, Inc., and dissolved in hexane. Elemol, which was identified as a major component of the Osage orange, was also purchased and dissolved in hexane. Specifically, technical grade elemol (assayed at 55%), from Augustus Oils LTD, Borden, Hampshire, UK, was used because elemol at higher purity levels was not available at the time of testing.

Isolation Methods

Steam distillation. The steam distillation method followed Pavia et al., 1988, *Introduction to Organic Laboratory Techniques*, 3d ed. Seven ripe fruits were ground by using a hand-powered meat grinder and placed in a 5000-ml three-necked round-bottom boiling flask. Water was added to cover the fruit pieces and boiled for approximately three (3) hours, i.e., until approximately 500-ml of condensate was collected. The collected water was washed twice with 250-ml hexane, and the water discarded. The hexane washings were passed through anhydrous sodium sulfate to remove water. The hexane washing was tested without further purification or concentration. The collected hexane extract was analyzed by gas chromatography and chromatography/mass spectrometry to identify mixture components.

Methylene Chloride and Hexane Soxhiet Extractions. One ripe fruit was cut into several pieces about two (2) $cm^3$ in size, and placed into two separate Soxhlets. One apparatus was charged with 500-ml methylene chloride and the other with 500-ml hexane. The Soxhlets were heated to the boiling point of the respective solvents and allowed to cycle for approximately 24 hours. Particulates were removed from the solution by vacuum filtration and the water was removed by filtration with anhydrous sodium sulfate. The collected extract was tested without further purification or concentration.

Chopped and Ground Hexane Soaking Extractions. One ripe fruit was cut into pieces about two (2) $cm^3$ in size and soaked for 24 hr in 500-ml hexane Another fruit was ground by using a hand-powered meat grinder and soaked for approximately 24 hr in 500-ml hexane. Particulates were removed from the extracts by vacuum filtration and the water was removed by filtration with anhydrous sodium sulfate.

Figure 4:
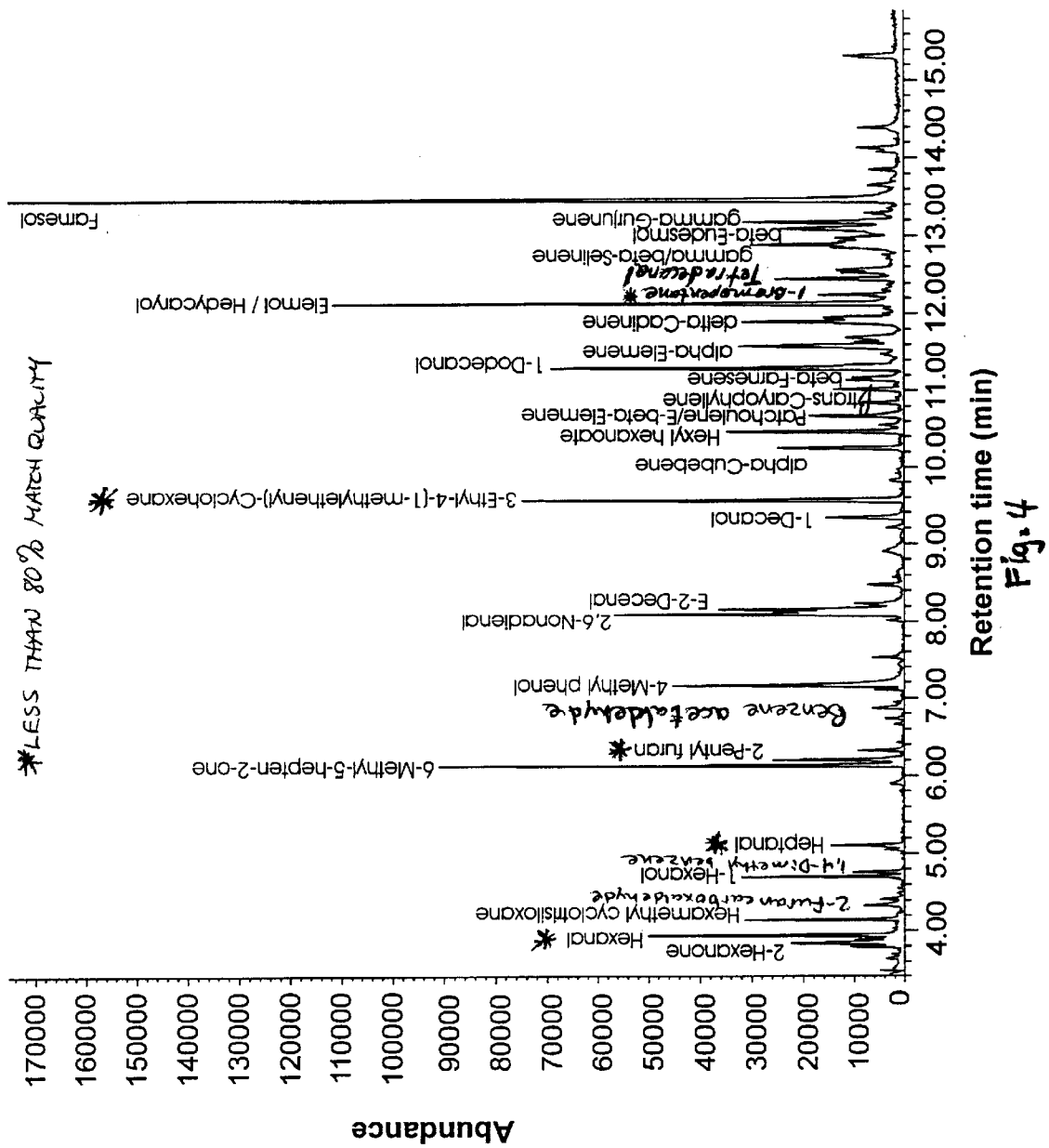
FIG. 4 shows a capillary gas chromatography ("GC") profile from volatiles collected from a steam distillate of a ripe Osage orange in abundance (of particles) versus retention time in minutes (mi). A labeled GC-peak indicates the volatile constituent was identified using mass spectrometry coupled with a GC retention time index.
Figure 5:
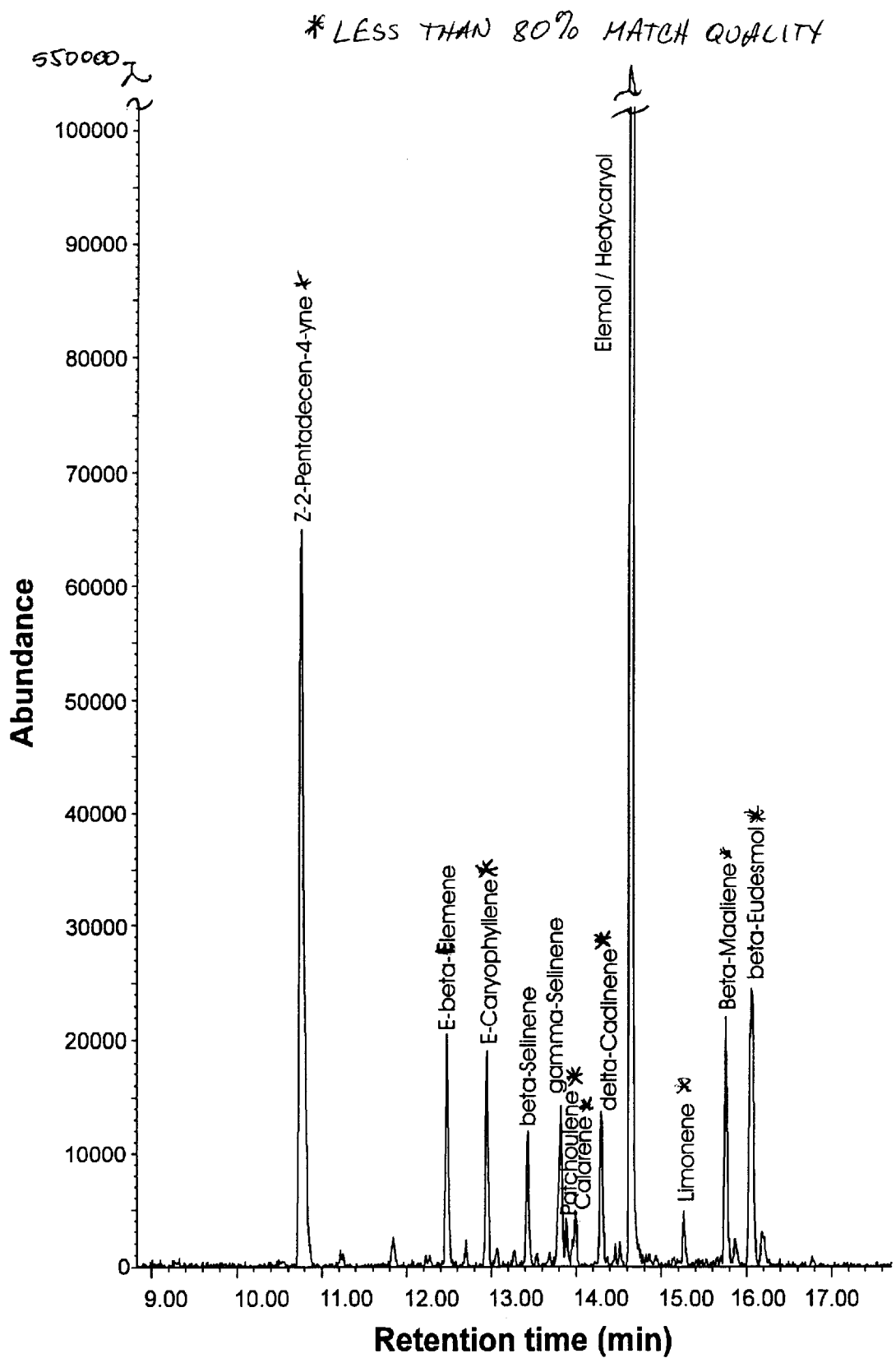
FIG. 5 shows a GC profile from volatiles collected from a steam distillate of an unripe Osage orange in abundance versus retention time (min). A labeled GC-peak indicates the volatile constituent was identified using mass spectrometry coupled with a GC retention time index.

Table 5 shows the constituents identified by using the above-described isolation methods together with GC-MS for a ripe Osage orange. FIGS. 4 and 5 shows a profile of the constituents identified (using GC-MS) in the extract from the steam distillation isolation method for the ripe and unripe Osage orange, respectively, with some of the peaks labeled accordingly. "Approximate Percent Relative Area" refers to the area under the "peak" of a particular component, i.e., a percent of the total response by the detector during analysis. Such percentage is not directly equivalent to a specific volume or weight percentage of a particular component in the test solution. Actual concentrations of the various components can be determined by correlating these results with the area percentages of known standards by constructing a "standard curve," as is known in the art. In some instances, the approximate percent relative area is not reported, and the likely presence or non-presence of a component in a particular extract is noted with a "+" or "−."

Retention times and, in some instances, relative area percentage, for components in the ripe steam distillate, chopped hexane soak, ground hexane soak, methylene chloride Soxhlet and hexane Soxhlet extracts can be seen in Table 5. The retention times and abundance of the components in the ripe steam distillate of the Osage orange can be seen in FIG. 4. Generally, a component is listed below without qualification if the match quality was greater than 80%. Those components marked with an asterisk had a match quality of less than 80%. "Match quality" is a term known in the art that refers to the level of overlap with regard to a number of criteria (e.g., molecular weight, similarity of major fragment, etc.) between the compound being tested and a library of the spectra of known compounds stored in a database. The match qualities during mass spectroscopy of the various components listed in Table 5 varied considerably. Therefore, although it is possible that the components listed with low match qualities are correctly identified, further testing needs to be performed to verify these results with more certainty.

TABLE 6

Constituents of ripe Osage orange identified using steam and solvent (FIG. 5)

| Retention Time (min) | Compound |
| --- | --- |
| 10.76 | Z-2-Pentadecen-4-yne* |
| 12.48 | E-beta-Elemene |
| 12.95 | E-Caryophyllene* |
| 13.44 | beta-Selinene |
| 13.8 | gamma-Selinene |
| 13.83 | Patchoulene* |
| 13.95 | Calarene* |
| 14.30 | delta-Cadinene* |
| 14.65 | Elemol/Hedycaryol |
| 15.25 | Limonene* |
| 15.76 | beta-Maaliene* |
| 16.06 | beta-Eudesmol* |

*Match quality is less than 80%.

TABLE 5

Constituents of ripe Osage orange identified using steam and solvent extraction methods

| | | Approximate Percent Relative Area | | | | |
| --- | --- | --- | --- | --- | --- | --- |
| Retention time (min.) | Compound | Steam Distillate (Ripe) FIG. 4 | Chopped Hexane Soak | Ground Hexane Soak | MeCl$_2$ Soxhlet | Hexane Soxhlet |
| 3.84 | 2-Hexanone | 1.2 | + | − | − | − |
| 3.94 | Hexanal* | + | − | − | − | − |
| 4.15 | Hexamethyl cyclotrisiloxane | 1.4 | − | + | − | − |
| 4.33 | 2-Furancarboxaldehyde | 0.6 | − | | | |
| 4.7 | 1-Hexanol | 1.1 | − | − | − | − |
| 4.76 | 1,4-Dimethyl benzene | 0.5 | − | − | − | − |
| 5.1 | Heptanal* | 0.5 | − | − | − | − |
| 6.13 | 6-Methyl-5-hepten-2-one | 3.8 | − | − | − | − |
| 6.2 | 2-Pentyl furan* | + | − | − | − | − |
| 6.87 | Benzene acetaldehyde | 0.5 | − | − | − | − |
| 7.16 | 4-Methyl phenol | 3.6 | − | + | − | − |
| 8.1 | 2,6-Nonadienal | 4.4 | − | − | − | − |
| 8.16 | E-2-Decenal | 2 | − | − | − | − |
| 9.34 | 1-Decanol | 0.9 | − | − | − | − |
| 9.57 | 3-Ethyl-4-(1-methyl-ethenyl)cyclohexane* | 5 | 1.1 | 2.5 | − | 1.2 |
| 10.26 | α-Cubebene | 1.7 | − | + | − | − |
| 10.47–10.5 | Hexyl hexanoate | + | 1.6 | 0.9 | − | − |
| 10.67 | Patchoulene/beta-Elemene | 1.2 | − | − | 0.4 | − |
| 11.01 | β-E-Caryophyllene | 0.9 | + | + | 0.2 | + |
| 11.17 | β-Farnesene | + | + | + | − | − |
| 11.3 | 1-Dodecanol | 4.8 | − | + | − | − |
| 11.58 | alpha-Elemene | 3.2 | − | 2 | − | − |
| 11.9 | δ-Cadinene | 2.5 | + | + | − | − |
| 12.13–16 | Elemol/Hedycaryol | 7.3 | 2 | 1.7 | 1.4 | 2.9 |
| 12.46 | 1-Bromo-pentane* | − | 0.8 | 1.6 | 0.5 | 0.6 |
| 12.56 | Tetradecanal | − | + | + | + | + |
| 12.89 | gamma/beta-Selinene | − | − | + | − | − |
| 13.09 | beta-Eudesmol | 3 | − | − | − | − |
| 13.17 | gamma-Gurjunene | 2.3 | − | + | − | − |
| 13.46–50 | Z,E-Farnesol | 13.6 | 3.8 | 9.4 | 1.7 | 1.6 |

*Match quality is less than 80%.
"+" Component is likely present in extract.
"−" Component is likely not present in extract.

Table 6 lists the components of the unripe steam distillate. The retention times and abundance of the components in the ripe steam distillate of the Osage orange can be seen in FIG. 5.

Solid-phase micro-extraction. To identify volatiles released from the Osage orange by other means, both ripe and unripe fruits were placed into separate one (1) liter glass containers. In this embodiment, head space volatiles were collected at room temperature by using a solid-phase micro-extraction (SPME) device, which contains a polymer fiber coated with approximately 100 μm of polydimethylsiloxane (Supelco Co., Bellefonte, Pa.). The SPME fiber was preconditioned for about two (2) hr at about 250° C. prior to volatile collection via exposure to the volatiles through a septum in the glass container. During the collection process, the fiber was exposed to and placed over the fruits in a glass container supplied with charcoal-filtered air at a flow rate of about 50 ml/minute. The collections continued for about 30 to 120 min, at which time the SPME fiber was immediately inserted into the injector of a GC-MC system for thermo-desorption. The GC-MS system was composed of a Hewlett Packard 5890 Series II gas chromatography equipped with a DB-5 column (30 m×0.25 mm inner diameter, J & W Scientific Co., Folsom, Calif.), and a Hewlett Packard 5972 Mass Selective Detector (MSD). The injector temperature was set at approximately 250° C. The split valve was opened approximately one (1) min after injection. The column temperature was initially about 40° C. for about one (1) min following the injection, then ramped to 250° C. at a rate of about 15° C./min. Mass spectra were recorded from 30 to 550 amu after electron impact ionization at 70 electron volts (eV).

Figure 6:
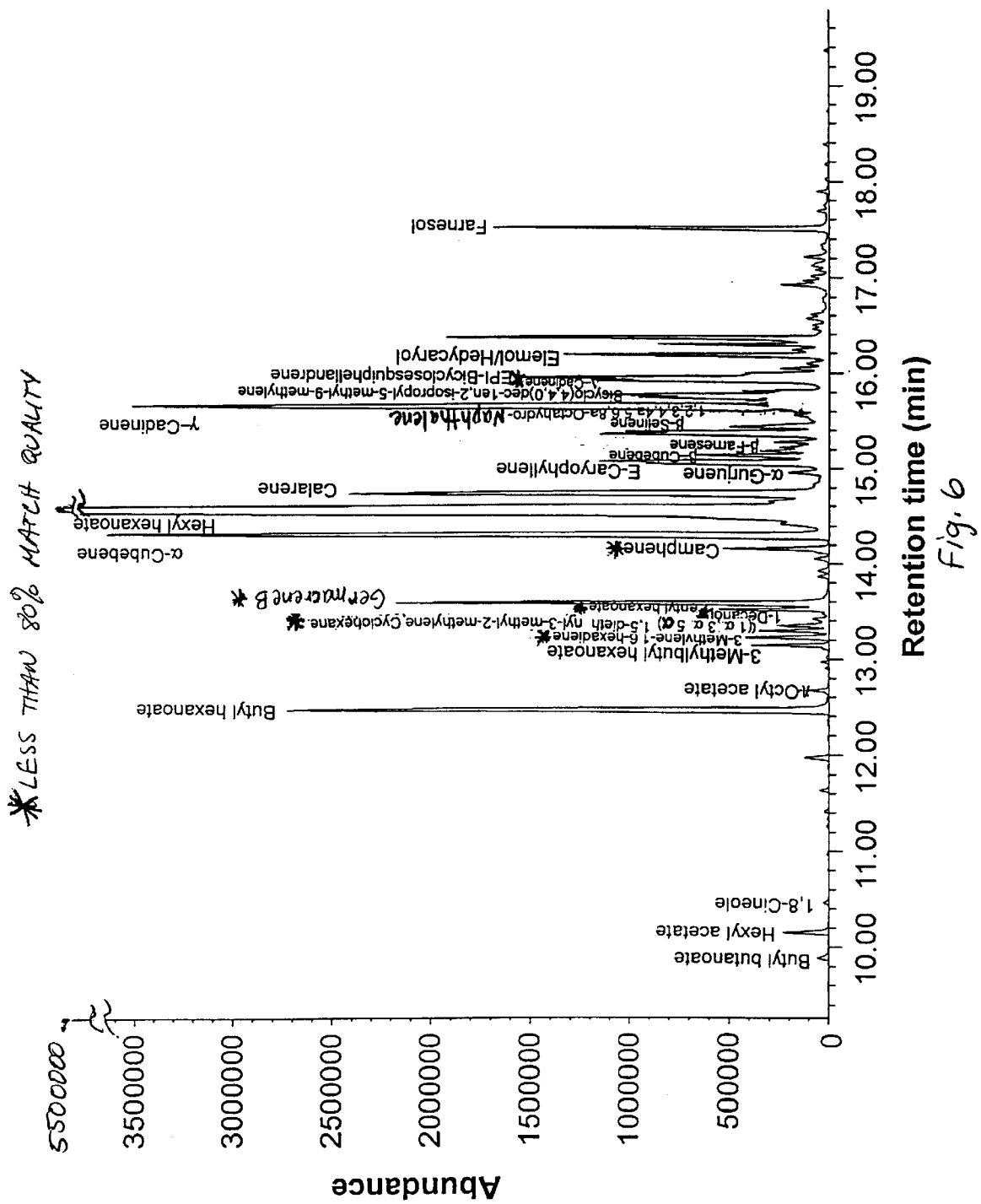
FIG. 6 shows a GC profile from volatiles collected from a solid-phase micro-extraction (SPME) of a ripe Osage orange in abundance versus retention time (min). A labeled GC-peak indicates the volatile constituent was identified using mass spectrometry coupled with a GC retention time index.
Figure 7:
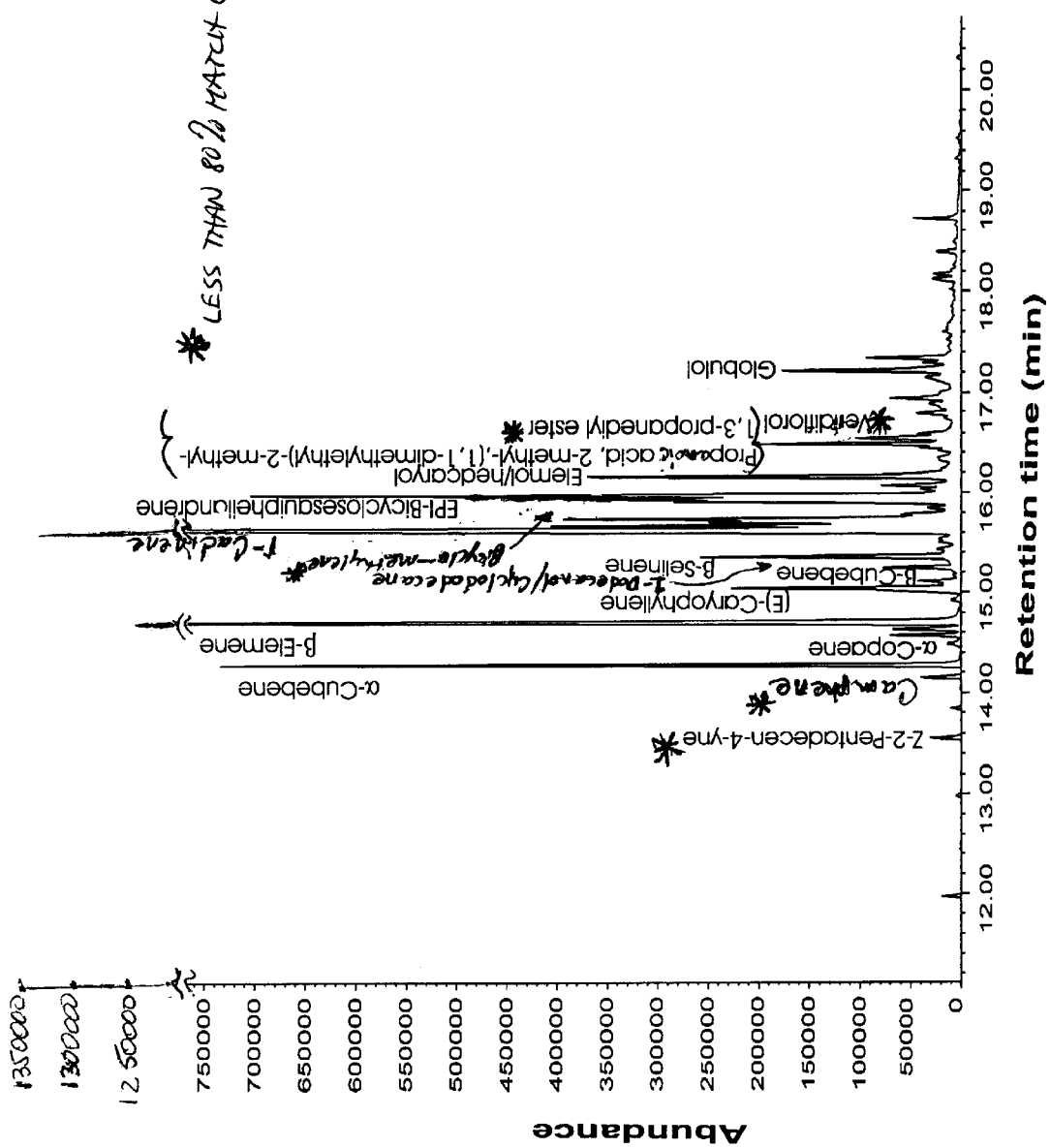
FIG. 7 shows a GC profile from volatiles collected from an SPME of an unripe Osage orange in abundance versus retention time (min). A labeled GC-peak indicates the volatile constituent was identified using mass spectrometry coupled with a GC retention time index.

Table 7 and FIGS. 6 and 7 show the constituents identified in ripe and unripe Osage orange in the SPME extract (using GC-MS) with some of the peaks labeled in the profiles.

TABLE 7

Identification of volatile constituents in Osage orange using SPME and GC-MS.

| Retention time (min.) | Compound | Unripe (cut) % Rel. Area | Unripe (intact) % Rel. Area FIG. 6 | Ripe (intact) % Rel. Area FIG. 7 |
| --- | --- | --- | --- | --- |
| 9.9 | Butyl butanoate | – | – | 0.3 |
| 10.16 | Hexyl acetate | – | – | tr |
| 10.47 | 1,8-Cineole | – | – | tr |
| 12.48 | Butyl hexanoate | – | – | + |
| 12.68 | n-Octyl acetate | – | – | 0.3 |
| 13.15 | 3-Methyl butyl hexanoate | tr | – | 0.7 |
| 13.23 | 3-Methylene-1,6-hexadiene* | – | – | + |
| 13.3 | (1α, 3α, 5α)1,5-Diethynl-3-methyl-2-methylene cyclohexane | – | – | + |
| 13.35 | 1-Decanol* | – | – | + |
| 13.52 | Pentyl hexanoate* | tr | – | 0.8 |
| 13.56 | Z-2-Pentadecen-4-yne* | – | + | – |
| 13.59 | Germacrene B* | – | + | + |
| 14.17 | Camphene* | 0.6 | 0.4 | 1 |
| 14.31 | α-Cubebene | 11 | 7.7 | 5 |
| 14.5–14.59 | Hexyl hexanoate | – | – | 30 |
| 14.56 | alpha-Copaene | – | + | – |
| 14.62–14.7 | β-Elemene | 17 | 14 | 4 |
| 14.74 | Calarene | – | – | + |
| 14.96 | α-Gurjuene | 0.2 | – | 0.3 |
| 15.07 | trans-Caryophyllene | 5.7 | 3.3 | 1.1 |
| 15.13 | β-Cubebene | – | + | 0.5 |
| 15.22 | β-Farnesene | – | – | + |
| 15.36 | 1-Dodecanol/Cyclododecane | – | 3.3 | – |
| 15.38 | β-Selinene | 4.4 | 0.6 | 3 |
| 15.56 | 1,2,3,4,4a,5,6,8a-Octahydro-Naphthalene | tr | – | 0.5 |
| 15.66 | gamma-Cadinene | 17 | 23 | 6 |
| 15.75 | Bicyclo (4,4,0)dec-1-3n,2-isopropyl-5-methyl-9-methylene* | 5 | 6 | 0.7 |
| 15.92 | δ-Cadinene* | – | – | 1.8 |
| 15.95 | EPI-Bicyclosesquiphellandrene | 3.8 | 7 | 2 |
| 16.18 | Elemol/Hedycaryol | 2.4 | 4 | 1.5 |
| 16.49 | Propanoic acid, 2-methyl-(1,1-dimethylethyl)-2-methyl-propanediyl ester* | – | + | – |
| 16.55 | Veridiflorol* | tr | 0.9 | – |
| 17.22 | Globulol | – | + | – |
| 17.52 | Farnesol | – | – | + |

*Match quality is less than 80%
"+" Indicates that a component is likely present in an extract.
"–" Indicates that a component is likely not present in an extract.

The above results show that different types and amounts of various components are present in a mature or ripe Osage orange as compared with an unripe Osage orange. However, there are a number of other components in both the ripe and unripe Osage orange that have not yet been identified. Further work to identify these components and verify the identification of components currently having a low match quality, using a combination of these and other techniques known in the art, will eventually yield the complete make-up of both the ripe and unripe Osage orange.

Testing Procedure. The same procedure described in Example 1 was used.

Results. The results of this testing are shown below in Table 8.

TABLE 8

Osage orange essential oil and Osage orange individual component repellency against the German cockroach as compared with naphthalene

| | Amount Used | Mean Treated (Seconds) | SEM | Mean Untreated (Seconds | SEM | % repellency* |
|---|---|---|---|---|---|---|
| Osage orange (unripe) | | | | | | |
| Steam Dist | 5 ml | 95.5 | 9.8 | 206 | 10.3 | 37 |
| | 1 ml | 78.3 | 12.6 | 223 | 12.2 | 48 |
| Osage Orange (ripe) | | | | | | |
| Steam Distillate | 1 ml | 64.8 | 20.2 | 235 | 20.2 | 57 |
| Ground Hexane Soak | 1 ml | 76.6 | 10.9 | 224 | 11 | 49 |
| Chopped Hexane Soak | 1 ml | 111 | 10 | 188 | 10.8 | 26 |
| Hexane Soxhlet | 1 ml | 85.5 | 13.6 | 208 | 13.1 | 42 |
| MeCl$_2$ Soxhlet | 1 ml | 116 | 10.5 | 184 | 10.3 | 23 |
| Osajin | 1% | 103 | 13 | 197 | 13.1 | 31 |
| | 0.5% | 117 | 11.6 | 184 | 12.2 | 22 |
| Pomiferin | 1% | 138 | 17.2 | 163 | 17.2 | 8.3 |
| Hexyl hexanoate | 1% | 142 | 5.9 | 158 | 5.7 | 5.2 |
| α-Cubebene | 0.5% | 99.4 | 14.6 | 211 | 15.9 | 36 |
| | 0.1% | 118 | 9.2 | 182 | 9.2 | 21 |
| Elemol (technical grade) ~55% pure | 1% | 107 | 12.1 | 196 | 11.9 | 30 |
| Naphthalene | 1% | 117 | 14.8 | 184 | 14.6 | 22 |

*Percent repellency was calculated by the following formula: (untreated − treated / 300) * 100

It should be noted that the concentration of essential oil for the unripe Osage orange steam distillate test solution was determined to be about 65 μg/one (1) ml. Specifically, through GC-MS, it was found that the concentration of elemol in the unripe steam distillate of the Osage orange was about 34 μg/ml. The percentage of elemol in the unripe steam distillate was determined to be approximately 52%. Because this 34 μg/ml was about 52% of the total unripe steam distillate, the concentration of the essential oil in the unripe steam distillate was estimated to be about 65 μg/ml. Because one (1) ml of the unripe steam distillate was applied to the filter paper in the assay, it is estimated that about 65 μg of essential oil was used in the apparatus. This indicates that the concentration of the essential oil on the filter paper was approximately 1.06 μg/cm$^2$.

As Table 8 shows, the sesquiterpenoids demonstrated repellency against the German cockroach. Specifically, alpha-cubebene demonstrated excellent repellency. Elemol also demonstrated very good repellency. However, it is known that the technical grade of elemol contains a significant amount of delta-codinene. Further repellency testing using a higher purity of elemol will likely yield different results.

Pomiferin and hexyl hexanoate are non-sesquiterpenoid components which performed relatively poorly, as the cockroaches appeared to be indifferent to these compounds at the concentrations tested. Osajin did demonstrate repellency against the German cockroach and may have some uses, perhaps in combination with one or more of the volatile sesquiterpenoids in the Osage orange. However, since osajin is not a volatile component, repellency is less effective, i.e., only via contact.

Conclusions

Testing to date shows that steam distillates of various ripe Osage orange components performed better than components extracted by other means. This includes, but is not limited to, alpha-cubebene, elemol, as well as the osajin. Further, components of the Osage orange not yet tested, particularly the volatile sesquiterpenoids, may also be effective repellents. It may also be that a combination or blend of the various constituents of the Osage orange, together with a suitable carrier, will provide even better repellency than any of the individual components can achieve alone. Future testing using various concentrations of DEET and other concentrations of napthelene as comparisons, is also expected to be performed.

EXAMPLE 3

The purpose of this experiment was to determine the means by which repellents, such as the various compounds tested in Example 1, are detected by an insect.

Materials and Methods

Insects. Cockroaches from the same source as in Examples 1 and 2 were used.

Standard and Comparison Compounds. DEET was purchased from Aldrich Chemicals.

Starting Materials. The steam distillate and purified isomers of catnip (nepetalactone) as described in Example 1 were used.

Testing Procedure. Male cockroaches were antennectomized by using a razor blade to remove the antennae as close to the head as possible. The cockroaches were allowed to recover from the procedure for 24 hours before being exposed to the test compounds in the bioassay described in Example 1.

Results. Comparisons between test compounds for the treated side were made using a paired t-test as shown in Table 9.

TABLE 9

Results of behavioral assay of antennectomized male cockroaches, and paired t-test comparison with non-antennectomized male cockroaches tested at the same concentration

| Treatment ($\mu g/cm^2$) | Mean seconds on treated side ± SEM | Calculated t-value | Mean seconds on untreated side |
|---|---|---|---|
| 1600 DEET | | | |
| Annectomized | 148 ± 17.1 | | 154 ± 17.2 |
| Non-antennectomized | 63.4 ± 15.9 | 3.03* | |
| 160 Z,E-Nepetalactone | | | |
| Annectomized | 121 ± 10.6 | | 180 ± 10.5 |
| Non-antennectomized | 65.4 ± 11.8 | 3.40* | |
| 80 E,Z-Nepetalactone | | | |
| Annectomized | 153 ± 15.2 | | 149 ± 15.3 |
| Non-antennectomized | 31.7 ± 5.2 | 7.84* | |

*Difference is significant by two-tailed paired t-test at $\alpha = 0.05$, df = 9.

The cockroaches without antennae were indifferent to the repellents tested, as they spent nearly equal amounts of time on both sides of the filter paper.

Conclusions

The results of this testing demonstrates that chemoreceptors responsible for the repellent action of the compounds are located on the antennae of the German cockroach. It is likely that such chemoreceptors are located on the antennae of other arthropods having antennae as well.

EXAMPLE 4

Testing methods and materials. In this experiment, female German cockroaches were tested in the same manner described in Example 1 against the steam distillates of catnip and the Osage orange. Testing using the commercial repellent, DEET, was also performed for comparison. It is known that male cockroaches are generally more sensitive to repellents, such as DEET, than female cockroaches. This testing was performed to determine if the test compounds would be similarly effective.

Results. Table 10 shows the commercial standard, DEET, as compared with acetone against the female German cockroach. "L" and "R" refer to left and right sides of the filter paper.

TABLE 10

Female German cockroach testing-10% *(1600 $\mu g/cm^2$) DEET vs. acetone

| trial | treated | untreated | treated on |
|---|---|---|---|
| 1 | 157 | 150 | L |
| 2 | 146 | 155 | L |
| 3 | 137 | 162 | R |
| 4 | 150 | 152 | L |
| 5 | 99 | 203 | R |
| 6 | 166 | 135 | L |
| 7 | 144 | 154 | L |
| 8 | 144 | 156 | R |
| 9 | 116 | 182 | R |
| 10 | 181 | 120 | L |
| mean | 144 | 156.9 | |
| SEM | 7.4 | 7.2 | |

*by volume

As can be seen, at the ten (10)% rate, DEET exhibits reduced repellency against female cockroaches as compared with the male cockroaches tested above since there was no significant difference between the treated and untreated sides. In comparison, the same ten (10)% DEET treatment resulted in 63 seconds on the treated side and 238 seconds on the untreated side as described in Example 1 (See Table 2).

Table 11 is a comparison of the essential oil of catnip, as compared with hexane against the female German cockroach.

TABLE 11

Female German cockroach testing-Five (5)%* (800 $\mu g/cm^2$) catnip steam distillate vs. hexane

| trial | treated | untreated | treated on |
|---|---|---|---|
| 1 | 107 | 197 | L |
| 2 | 80 | 221 | L |
| 3 | 90 | 212 | R |
| 4 | 67 | 235 | R |
| 5 | 86 | 217 | L |
| 6 | 210 | 91 | R |
| 7 | 127 | 174 | L |
| 8 | 163 | 139 | R |
| 9 | 120 | 182 | R |
| 10 | 89 | 212 | R |
| mean | 113.9 | 188 | |
| SEM | 13.8 | 13.9 | |

*by volume

The results shown in Table 11 demonstrate a very high repellency of the essential oil of catnip, i.e., nepetalactone, against the female German cockroach in many of the trials. Unlike DEET, however, which showed no significant repellancy against female German cockroaches, the essential oil of catnip demonstrated very good repellency at the lower rate of about five (5)%.

Table 12 is a comparison of the essential oil of the ripe Osage orange with hexane against the female German cockroach.

TABLE 12

Female German cockroach testing-Two (2) ml ripe Osage orange steam distillate vs. hexane

| trial | treated | untreated | treated on |
|---|---|---|---|
| 1 | 109 | 193 | R |
| 2 | 118 | 186 | R |
| 3 | 138 | 166 | R |
| 4 | 138 | 166 | L |
| 5 | 153 | 148 | L |
| 6 | 151 | 153 | L |
| 7 | 150 | 151 | L |
| 8 | 122 | 184 | R |
| 9 | 131 | 172 | L |
| 10 | 63 | 239 | R |
| mean | 127.3 | 175.8 | |
| SEM | 8.5 | 8.5 | |

Again, in many of the trials, the essential oil of the Osage orange performed surprisingly well, exhibiting very good repellency against the female cockroach.

Conclusions

Several of the compounds and extracts tested performed better than the commercial standard, DEET, with regard to repellency against female cockroaches. These tests show that female cockroaches can be repelled by the essential oils of catnip and the Osage orange (although not to the same extent as the males). This is in accord with Scheffler and Dombrowski, 1992, *Insecticides: Mechanism of Reaction and Resistance,* Andover, U. K. These results indicate that compositions containing nepetalactone or, likely, one of its isomers, as well many of the components of the Osage orange, such as elemol, will likely be effective for use as an arthropod repellent, such as against the German cockroach.

EXAMPLE 5

The purpose of this test was to determine a non-lethal dose of nepetalactone to two mosquito species, for use in the activity chamber described in Example 7.

Insects. Mixed sexes of wild *Aedes aegypti* collected initially in Costa Rica in 1999 were used in this testing. Mixed sexes of *Culex tarsalis* mosquitoes obtained from the University of California at Berkley, in Berkley, Calif., were also tested. Both types of mosquitoes are now maintained in the Entomology Department at Iowa State University, Ames, Iowa according to the following methods of rearing:

*Aedes aegypti.* Eggs from the mosquitoes are dried and stored in plastic bags in a refrigerator for several months. The date of storage is noted on the container. A section of paper towel containing the oldest eggs are then placed in deoxygenated water. Larvae typically emerge in minutes. Once the larvae have emerged, they are placed into a pan having about 2.5 to 3.7 cm (about one (1) to 1.5 in) of water. Two (2) to three (3) drops of Tetramin™ mix is added and the pans are labeled with the appropriate date. Tetramin™ is made by TetraWerke in Melle, Germany, and distributed in the United States by the Tetra Co. in Blacksburg, Va. One drop of Tetramin™ mix is added everyday until the larvae reach the third instar. The larvae are fed about one (1) to three (3) drops of Tetramin™ mix daily, depending on their progression of growth. If growth is poor, more drops are given. Fifty pupae are then collected in cups that are half-filled with distilled water. The cup is properly labeled and sealed with a mesh square and lid. A sucrose-saturated cotton ball is then placed on the mesh and flattened. After emergence of all mosquitoes in the cup, the mosquitoes are released into a labeled cage. A sedated live rabbit is placed on top of the cage about six (6) to seven (7) days after release for the mosquitoes to feed on for 15 to 20 minutes. Three days after feeding, a cup that is about half-full with distilled water and lined with a paper towel (i.e., oviposition dish) is placed in the cage. After two days, the cup is removed and the paper is dried to start the cycle again.

Culex tarsalis. Five (5) egg rafts are placed in a pan having about 2.5 to 3.7 cm (about one (1) to 1.5 in) of water. About two (2) to three (3) drops of Tetramin™ mix is added daily. Pans are checked daily for hatching. Typically, the first instars appear in about two (2) to three (3) days. One (1) drop of Tetramin™ mix is added every day until the larvae reach the third instar. One (1) to three (3) drops of mix is fed to the larvae daily, depending on progression of growth. Fifty pupae are collected in cups in cups that are half-filled with distilled water. The cup is properly labeled with date, species, number of pupae, etc. The cup is then sealed with a mesh square and lid. (Green tape is used to indicate anautogenous, with red tape used for autogenous). A sucrose-saturated cotton ball is then placed on the mesh and flattened. After emergence of all mosquitoes in the cup, the mosquitoes are released into a labeled cage. A sedated quail is placed on top of the cage about six (6) to seven (7) days after release for the mosquitoes to feed on for about 15–20 minutes. The sucrose pads are removed the day before feeding. Three days after feeding, the oviposition dish (described above) is placed in the cage. The dish is removed after two days, and egg rafts are separated to five (5) per pan to start the cycle again. If necessary, mosquitoes can be fed on quail again three (3) to four (4) days after oviposition.

Standards and Starting Materials. The essential oil of catnip isolated as described above was used in this test. Hexane, purchased from Fischer Scientific, Inc., was used as a control.

Test Procedure. Toxicity tests were conducted in the upper sections of a number of glass bottles. Specifically, each glass bottle was cut into two sections, and the bottom portion was discarded. The remaining upper portion had a volume of approximately 175-ml. The top of the upper portion had a ground glass mouth. The open bottom end was covered with a seven (7)-cm piece of filter paper, which was secured with all-purpose glue. The glue was allowed to dry and excess filter paper was trimmed by using a razor blade. One-half ml of hexane solution was applied to the filter paper. The hexane was allowed to dry for approximately one (1) minute. Parafilm® brand paraffin stretch wrap film made by American National Can Co. in Chicago, Ill., was placed on the outside of the bottle to seal the bottom of the bottle over the filter paper. Approximately five (5) adult mosquitoes (mixed sexes) were placed in the bottle through the mouth. The mouth was then plugged with a cotton ball that had been soaked in a ten (10)% sucrose solution. Mortalities were recorded at 0.5, 24, 48 and 120 hours.

Results. The results of this testing are shown in Table 13.

TABLE 13

Mosquito mortality at varying concentrations of nepetalactone derived from catnip

| Catnip essential oil concentration | % Mortality | | | |
|---|---|---|---|---|
| ($\mu g/cm^2$) | 0.5 hr | 24 hr | 48 hr | 120 hr |
| *Aedes aegypti* | | | | |
| 130 | 26 | 100 | 100 | 100 |
| 65 | 37 | 100 | 100 | 100 |
| 13 | 3 | 100 | 100 | 100 |
| 6.5 | 3 | 24 | 27 | 27 |
| 1.3 | 0 | 3 | 3 | 3 |
| Hexane control | 4 | 7 | 7 | 7 |
| Blank control | 0 | 10 | 10 | 10 |
| *Culex tarsalis* | | | | |
| 65 | 0 | 100 | 100 | 100 |
| 13 | 0 | 100 | 100 | 100 |
| 6.5 | 0 | 50 | 61 | 93 |
| 1.3 | 0 | 19 | 31 | 69 |
| Hexane control | 0 | 20 | 20 | 36 |

The above results demonstrate that the individual isomers of catnip as well as the essential oil of catnip, are each toxic to adult mosquitoes in a closed system. Such results could be due to fumigation or to contact toxicity.

Conclusion

Studies undertaken to determine sub-lethal concentrations of nepetalactone yielded surprisingly high toxicity in contact/fumigation bioassays.

EXAMPLE 6

This test will be conducted to study the repellency of mosquitoes in a static air environment, at concentrations that are nonlethal.

Insects. The two species of mosquitoes reared as described in Example 5 will be tested. The mosquitoes will be sexed and only female mosquitoes tested. This is because male mosquitoes do not bite and are not typically targeted by repellents, as they are not considered a risk for carrying disease. (i.e., most commercial repellents also target only female mosquitoes).

Standards and Starting Materials. The same standards and starting materials as described in Example 5 will be used.

Test procedure. A 61-cm (24 in) glass tube having a nine (9) cm inner diameter will be used. A hole will be cut in approximately the mid-point of the tube for central introduction of the mosquitoes. The tube will be marked into eight 7.6 cm sections along its length. Approximately one (1) ml of the test compound dissolved in hexane will be placed on a piece of filter paper about nine (9) cm in diameter. The hexane will be allowed to evaporate for approximately one (1) minute. The filter papers will be placed inside the lid of a nine (9) cm plastic Petri dish, and the lids placed over the ends of the glass tube. One end of the tube will be randomly selected to contain the test compound, while the other end will contain the appropriate solvent control. Approximately 20 female mosquitoes will be placed in the tube. The number of mosquitoes in each three (3) inch section of the tube will be counted at two (2) minute intervals for a total of ten (10) minutes. It is expected that the mosquitoes will spend less time in the area of the tube containing the test compound.

EXAMPLE 7

The repellency of many or all of the terpenoids described in all of the previous Examples will be tested with a variety of methods against mosquitoes maintained in the manner described in Example 5. Two of these methods are described below. The first method ("Y-Tube Olfactometer Method") will measure repellency by determining if the mosquitoes will reject an otherwise attractive odor source (e.g., lactic acid), when the attractive odor is mixed with a repellent. The second test ("Computerized Insect Activity Chamber Method") will measure changes in spontaneous activity of mosquitoes exposed to the repellents. Again, in both methods, only female mosquitoes will be tested.

Testing Procedure. Y-Tube Olfactometer Study for Mosquito Repellency. This method follows, with modification, the method reported by Mauer and Rowley, 1999, *Journal of Medical Entomology*, 35(4): 503–507. A dual-port olfactometer will be used to measure whether or not female mosquitoes will reject an otherwise attractant odor source when mixed with a repellent. Lactic acid will be used as the attractant odor source. The mosquitoes will be given a choice, in the olfactometer, of following an air stream containing lactic acid alone, or lactic acid mixed with a test compound. Approximately two (2) ml of test compound solution will be applied to a filter paper and the solvents allowed to evaporate. The filter paper will then be placed into a randomly chosen arm of the Y-tube. After approximately 30 minutes in the apparatus, the number of mosquitoes in each arm will be counted. It is expected that the insects will reject the air streams containing the repellent compositions.

Computerized Insect Activity Chamber Method. This method, which measures spontaneous activity of mosquitoes, follows the procedure described in Rowley et al., "A microcomputer-monitored mosquito fight activity system," *Annals of the Entomological Society of America*, 80: 534–538 (1987). The repellent compounds are placed onto a filter paper at the bottom of the chamber. A female mosquito is placed into an activity chamber and the computer records the number of flights, length of flights, and the time of day the insects flew. After several days of collection, the activity spectra will be compared and differences in spontaneous activity will be sought. It is expected that the spontaneous activity of the mosquitoes will be different in the treated groups as compared with the control groups.

The ability of a compound to repel other arthropods (e.g. houseflies, gnats, spiders, ticks, mites, and so forth) can be determined using assay methods that are well-known in the art These novel repellents will be useful in many applications, including indoor and outdoor residential use, veterinary applications, commercial pest control for livestock, in shipping containers, and so forth. Such repellents can be used in a wide range of target areas, including, for example, a garden, lawn, tent, barn, house or commercial building. Such repellents can also be used on a human or animal.

The terpenoids described in this invention are able to repel target pests, in many instances, better than known commercial standards. Preferred terpenoids possess slight volatility, thus increasing their efficacy. The repellents can be applied by any suitable delivery means, including, but not limited to, broadcast or restricted localized spraying, chemigation, use of a controlled-release point-source dispenser as well as use of creams, liquid-based products, powders, and so forth. The Applicants have further identified, for the first time, many of the components present in the Osage orange, and plan to identify the complete profile. Applicants have also determined that repellents are detected via the antennae of the target pest. Furthermore, the biorational repellents of the present invention are generally less toxic than conventional non-biorational repellents, such as DEET.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A repellent composition comprising an effective repellent amount of Z,E-nepetalactone to repel a target pest from a target area, the Z,E-nepetalactone in combination with a carrier.

2. The composition of claim 1 wherein the carrier is a liquid, solid or gas.

3. The composition of claim 1 wherein the target pest is an arthropod selected from the group consisting of cockroaches, mosquitoes, black flies, house flies, gnats, stored grain pests, moths, ticks, mites and spiders.

4. The composition of claim 3 wherein the target area is a human or animal.

5. The composition of claim 3 wherein the target area is out-of-doors or indoors.

6. The composition of claim 1 wherein the Z,E-nepetalactone is an individual isomer of a plant volatile selected from the group consisting of *Nepeta mussini*, *Nepeta grandiflora*, *Nepeta nuda* and a combination thereof.

7. The composition of claim 2 wherein the carrier is selected from the group consisting of oils, polymers, plastics, waxes, wood, gels, colloids, granular materials, dusts, powders, sprays, drenching means, emulsifiable concentrates, and any combination thereof.

8. The composition of claim 4 wherein the target area is clothing.

9. The composition of claim 4 wherein the animal is a pet or livestock.

10. The composition of claim 5 wherein the target area is selected from the group consisting of a garden, yard, plant, camping area, tent, bed net, sleeping bag, body of water, park, field, barn, garage, commercial building, private building, home, cupboard, shipping container, packing material, and bedding.

* * * * *

UNITED STATES PATENT AND TRADEMARK OFFICE
CERTIFICATE OF CORRECTION

PATENT NO.       : 6,524,605 B1
DATED            : February 25, 2003
INVENTOR(S)      : Joel R. Coats et al.

It is certified that error appears in the above-identified patent and that said Letters Patent is hereby corrected as shown below:

<u>Title page,</u>
Item [56], References Cited, OTHER PUBLICATIONS, insert the following:
-- Black, J.W., "Nepetalactone: scores purrfect with cats!", *Chem 13 News,* 12-13, (Jan. 1995).
Das, Y., et al., "Non-Repellency of Two Insect Growth Regulators with Juvenile Hormone Activity to *Blattella Germanica", Ent. exp. & appl.* 20, *North-Holland Publ. Co. Amsterdam,* 195-198, (1976).
Davis, E.E., et al., "Lactic Acid-sensitive Receptors on the Antennae of the Mosquito, *Aedes aegypti", J. comp. Physiol.- A,* 105, 43-54, (1976).
Eisenbraun, E.J., et al., "Structure and Stereochemistry of 4a$\beta$,7$\alpha$,7a$\beta$-Nepetalactone from *Nepeta mussini* and Its Relationship to the 4a$\alpha$,7$\alpha$,7a$\alpha$- and 4a$\alpha$,7$\alpha$,7a$\beta$-Nepetalactones from *N. cataria*", *J. Org. Chem.,* 45, 3811-3814, (1980).
Handjieva, N.V., et al., "Constituents of Essential Oils from *Nepeta cataria* L., *N. grandiflora* M.B. and *N. nuda* L.", *J. Essent. Oil Res.,* 8, 639-643, (Nov/Dec. 1996).
Jain, T.C., et al., "Thermolysis of Elemol Silver (I) Ion Catalyzed Conversion of Elemol to Eudesmols", *Tetrahedron Letters,* No. 50, *Pergamon Press,* 5139-5142, (1972).
Lindsay, L.R., et al., "Evaluation of the Efficacy of 3% Citronella Candles and 5% Citronella Incense for Protection Against Field Populations of *Aedes* Mosquitoes", *Journal of the American Mosquito Control Association,* 293-294, (1996).
Maugh, T.H., "To Attract or Repel, That is the Question", *Science,* Vol. 218, One page, (Oct. 15, 1982).
New uses for catnip oil, repelling mosquitoes!", <u>http://www.kookykat.com/new page l.htm</u>, pp. 1-5, (1995).
Osimitz, T.G., et al., "The Present Safety Assessment of DEET". *Journal of the American Mosquito Control Association,* 274-278, (1995)., and
Roland, E.H., et al., "Toxic encephalopathy in a child after brief exposure to insect repellents", *Can Med Assoc J,* Vol. 132, 155-156, (Jan. 15, 1985). --

UNITED STATES PATENT AND TRADEMARK OFFICE
CERTIFICATE OF CORRECTION

PATENT NO. : 6,524,605 B1
DATED : February 25, 2003
INVENTOR(S) : Joel R. Coats et al.

It is certified that error appears in the above-identified patent and that said Letters Patent is hereby corrected as shown below:

Column 2,
Line 43, delete "(mi)" and insert -- (min) -- therefor.

Column 6,
Line 11, insert -- " -- after "E,Z-isomer".
Line 17, delete "(4H)" and insert -- (4aH) -- therefor.

Column 10,
Line 29, delete "E,Z isomer" and insert -- E,Z-isomer -- therefor.
Line 45, delete "." before "6%".

Column 11,
Line 4, delete "gennanica" and insert -- germanica -- therefor.

Column 12,
Line 3, insert -- to -- after "converted".
Line 17, delete "R." and insert -- B. -- therefor.
Line 65, delete "." after "α=0.05" and insert -- , -- therefor.

Column 14,
Line 33, delete "Soxhiet" and insert -- Soxhlet -- therefor.
Line 44, insert -- . -- after "hexane".

Column 17,
Line 61, delete "30 mx0.25 mm" and insert -- 30 m x 0.25 mm -- therefor.

Column 23,
Line 52, delete "in cups" before "that".

UNITED STATES PATENT AND TRADEMARK OFFICE
CERTIFICATE OF CORRECTION

PATENT NO. : 6,524,605 B1
DATED : February 25, 2003
INVENTOR(S) : Joel R. Coats et al.

It is certified that error appears in the above-identified patent and that said Letters Patent is hereby corrected as shown below:

Column 25,
Line 67, insert -- . -- after "art".

Signed and Sealed this

Ninth Day of September, 2003

JAMES E. ROGAN
*Director of the United States Patent and Trademark Office*